(12) United States Patent
Aime et al.

(10) Patent No.: US 10,328,162 B1
(45) Date of Patent: Jun. 25, 2019

(54) CEST SYSTEMS EXHIBITING A CONCENTRATION INDEPENDENT RESPONSIVENESS

(71) Applicant: BRACCO IMAGING S.P.A., Milan (IT)

(72) Inventors: Silvio Aime, Carignano (IT); Daniela Delli Castelli, Bibiana (IT); Franco Fedeli, Vimodrone (IT); Dario Livio Longo, Manta (IT); Enzo Terreno, Bibiana (IT); Fulvio Uggeri, Codogno (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 16/256,749

(22) Filed: Jan. 24, 2019

Related U.S. Application Data

(62) Division of application No. 13/879,083, filed as application No. PCT/EP2011/069406 on Nov. 4, 2011, now Pat. No. 10,232,060.

(30) Foreign Application Priority Data

Nov. 5, 2010 (EP) .................................... 10190161

(51) Int. Cl.
*A61B 5/055* (2006.01)
*A61K 49/10* (2006.01)
*G01R 33/56* (2006.01)

(52) U.S. Cl.
CPC .......... *A61K 49/106* (2013.01); *A61K 49/101* (2013.01); *A61K 49/108* (2013.01); *G01R 33/5601* (2013.01)

(58) Field of Classification Search
None
See application file for complete search history.

(56) References Cited

U.S. PATENT DOCUMENTS

| 5,980,864 | A  | 11/1999 | Platzek et al. |
| 6,399,043 | B1 | 6/2002  | Platzek et al. |
| 2005/0191243 | A1 | 9/2005 | Aime et al. |
| 2007/0292354 | A1 | 12/2007 | Port |
| 2009/0196830 | A1 | 8/2009 | Lamerichs et al. |

FOREIGN PATENT DOCUMENTS

| EP | 0448191 A1 | 9/1991 |
| EP | 1331012 A1 | 7/2003 |
| EP | 1466629 A1 | 10/2004 |
| EP | 2067485 A1 | 6/2009 |
| JP | 2005515842 | 6/2005 |
| JP | 2008513533 | 5/2008 |
| WO | 2000066180 A2 | 11/2000 |
| WO | 2002043775 A2 | 6/2002 |
| WO | 2003063912 A1 | 8/2003 |
| WO | 2006032705 A2 | 3/2006 |
| WO | 2009072079 A2 | 6/2009 |

OTHER PUBLICATIONS

Aime, Silvio et al., "Iopamidol: Exploring the Potential Use of a Well-Established X-Ray Contrast Agent for MRI", Magnetic Resonance in Medicine, 2005, vol. 53, pp. 830-834, Wiley-Liss, Inc., www.interscience.wiley.com.
Aime, Silvio et al., "Novel pH-Reporter MRI Contrast Agents", Angewandte Chemie Int. Ed., 2002, vol. 41, No. 22, pp. 4334-4336, Wiley-VCH Verlag GmbH & Co. KGaA, Weinheim.
Aime, Silvio et al., "Paramagnetic Lanthanide(III) Complexes as pH-Sensitive Chemical Exchange Saturation Transfer (CEST) Contrast Agents for MRI Applications", Magnetic Resonance in Medicine, 2002, vol. 47, pp. 639-648, DOI 101002/mrm.10106, Wiley-Liss Inc.
Aime, Silvio et al., "Supramolecular Adducts between Poly-L-arginine and [Tmllldotp]: A Route to Sensitivity-Enhanced Magnetic Resonance Imaging-Chemical Exchange Saturation Transfer Agents", Angewandte Chemie Int. Ed., 2003, vol. 42, pp. 4527-4529, DOI:10.1002/anie.200352132, Wiley-VCH Verlag GmbH & Co. KGaA, Weinheim, www.angewandte.org.
Anantanarayan, Ashok et al., "Synthesis of a Dithia-18-crown-6-tetracarboxylic Acid", Journal Organic Chemistry, 1986, vol. 51, No. 5, pp. 752-755, American Chemical Society.
Balaban, Robert S., "Magnetization Transfer between Water and Macromolecules in Proton MRI", Section: Relaxometry and Related Topics, Editor: IR Young, Methods in biomedical magnetic resonance imaging andspectroscopy, vol. I. Chichester, UK, John Wiley & Sons; 2000, pp. 661-666.
Barge, Alessandro et al., "How to determine free Gd and free ligand in solution of Gd chelates. A technical note", Contrast Media & Molecular Imaging, 2006, vol. 1, pp. 184-188, Wiley InterScience, www.interscience.wiley.com, DOI:10.1002/cmmi.110.
Caravan et al. (Chem. Rev. 1999, 99, 2293-2352).
Corsi, Daniele M. et al., "Determination of paramagnetic lanthanide(III) concentrations from bulk magneticsusceptibility shifts in NMR spectra", Magnetic Resonance in Chemistry, 2001, vol. 29, pp. 723-726, John Wiley &Sons, Ltd.
Genina Crich, Simonetta et al., "In Vitro and in Vivo Magnetic Resonance Detection of Tumor Cells by TargetingGlutamine Transporters with Gd-Based Probes", Journal of Medicinal Chemistry, 2006, vol. 49, No. 16, pp. 4926-4936,American Chemical Society.
Goffeney, Nicholas et al., "Sensitive NMR Detection of Cationic-Polymer-Based Gene Delivery Systems Using Saturation Transfer via Proton Exchange", Journal American Chemical Society, 2001, vol. 123, No. 35, pp. 8628-8629.

(Continued)

*Primary Examiner* — Johann R Richter
*Assistant Examiner* — Melissa J Perreira
(74) *Attorney, Agent, or Firm* — Vivicar Law, PLLC

(57) ABSTRACT

The present invention relates to the use of non-equivalent mobile protons belonging to NMR distinguishable steroisomers of a CEST agent in a ratiometric based CEST imaging procedure and to Lanthanide (III) complex compounds displaying at least two NMR-distinguishable steroisomers in solution useful as concentration independent CEST responsive agents.

2 Claims, 21 Drawing Sheets

(56) References Cited

OTHER PUBLICATIONS

Huang. Ching-Hui et al., "Cerium( III), Europium( III), and Ytterbium(III) Complexes with Alchol Donor Groups asChemical Exchange Saturation Transfer Agents for MRI", Inorganic Chemistry, 2009, vol. 48, No. 15, pp. 7237-7243, DOI:10.1021/ic9006961, American Chemical Society.
Intention to Grant European application No. 11 778 892.7, dated Feb. 28, 2017.
Jacques, Vincent et al., "New Classes of MRI Contrast Agents", Topics in Current Chemistry, 2002, vol. 221, pp. 123-164, Springer-Verlag Berlin Heidelberg.
Kumar, Krishan et al., "Synthesis, Stability, and Structure of Gadolinium(III) and Yttrium( III) Macrocyclic Poly( amino carboxylates)", Inorganic Chemistry, 1994, vol. 33, No. 16, pp. 3567-3575, American Chemical Society.
Langereis, Sander et al., "A Temperature-Sensitive Liposomal 1H CEST and 19F Contrast Agent for MR Image-Guided Drug Delivery", Journal of the American Chemical Society, 2009, vol. 131, No. 4, pp. 1380-1381, ACS Publications.
Office Action for Australian application No. 2011325112, dated Feb. 10, 2015.
Office Action for Canadian application No. 2.816,948, dated Apr. 8, 2014.
Office Action for Canadian application No. 2.816,948, dated Feb. 10, 2015.
Office Action for Chinese application No. 201180053033.7, dated May 12, 2014 (English translation).
Office Action for Chinese application No. 201180053033.7, dated Mar. 30, 2016 (English translation).
Office Action for Chinese application No. 201180053033.7, dated Oct. 26, 2015 (English translation).
Office Action for Chinese application No. 201180053033.7. dated Mar. 27, 2015 (English Translation).
Office Action for European application No. 11 778 892.7. dated Sep. 2, 2015.
Office Action for Israeli application No. 226,123, dated Apr. 26, 2015 (English translation).
Office Action for Japanese application No. 2013-537145, dated Apr. 26, 2016 (English translation).
Office Action for Japanese application No. 2013-537145, dated Jul. 28, 2015 (English translation).
Office Action for Japanese application No. 2013-537145, dated Aug. 16, 2016 (English translation).
Office Action for Mexican application No. 2013/004825, dated Mar. 15, 2017 (English translation).
Office Action for Mexican application No. 2013/004825, dated Nov. 18, 2016 (English translation).
Office Action for Russian application No. 2013125778, dated Feb. 24, 2016 (English translation).
Office Action for Russian application No. 2013-125778, dated Oct. 29, 2015 (English translation).
Parker et al., "Being Excited by Lanthanide Coordination Complexes: Aqua Species, Chirality, Excited-State Chemistry, and Exchange Dynamics," Chem. Rev. 102:1977-2010 (2002).
PCT International Preliminary Report on Patentability for PCT application No. PCT/EP2011/069406. dated May 16, 2013.
PCT international Search Report for PCT/EP2011/069406, dated Jan. 31, 2012.
PCT Written Opinion for PCT/EP2011/069406, dated Jan. 31, 2012.
Ranganathan, Ramachandran S. et al, "New Multimeric Magnetic Resonance Imaging Agents", Investigative Radiology, vol. 33, No. 11,Nov. 11, 1998, pp. 779-797, XP001010000.
Stancanello, J. et al., "Development and validation of a smoothing-splines-based correction method for Improvingthe analysis of CEST-MR images", Contrast Media & Molecular Imaging, 2008, total pp. 14, Wiley InterScience, www.interscience.wiley.com.
Terreno, Enzo et al., "Ln(III)-DOTAMGiy Complexes: A Versatile Series to Assess the Determinants of the Efficacy of Paramagnetic Chemical Exchange Saturation Transfer Agents for Magnetic Resonance Imaging Applications", Investigative Radiology, 2004, vol. 39, No. 4, pp. 235-243, Lippincott Williams & Wilkins.
Terreno, Enzo et al., "Methods for an improved detection of the MRI-CEST effect", Contrast Media & Molecular Imaging, 2009, pp. 237-247, John Wiley & Sons, Ltd., www.interscience.wiley.com.
Viswanathan, Subha et al., "Alternatives to Gadolinium-Based Metal Chelates for Magnetic Resonance Imaging", Chemical Reviews, 110(5):2960-3018 (2010), American Chemical Society.
Ward, K.M. et al., "Determination of pH Using Water Protons and Chemical Exchange Dependent Saturation Transfer (CEST)", Magnetic Resonance in Medicine, vol. 44, Jun. 19, 2000, pp. 799-802, XP000969765, Academic Press, Duluth, MN, US, ISSN: 0740-3194.
Woods, et al., "Correlation of water exchange rate with isomeric composition in diastereoisomeric gadolinium complexes of tetra(carboxyethyl)dota and related macrocyclic ligands," J. Am. Chem. Soc. 122:9781-9792 (2000).
Woods, Market al., "Europium(III) Macrocyclic Complexes with Alcohol Pendant Groups as Chemical Exchange Saturation Transfer Agents", J. Am. Chem.. Soc., vol. 128, No. 31,Jul. 14, 2006, pp. 10155-10162, XP002621185.
Wu, Yunkou et al., "A Responsive Europium(III) Chelate That Provides a Direct Readout of pH by MRI", J. Am. Chem.. Soc., vol. 132, No. 40, Jul. 8, 2010, pp. 14002-14003, XP002622605.
Zhang, Shanrong et al., "A Novel Europium(III)-Based MRI Contrast Agent", J. Am. Chem. Soc., 123(7):1517-1518 (2001) American Chemical Society.
Zhang, Shanrong et al., "The Amide Protons of an Ytterbium(III) dota Tetraamide Com lex Act as Efficient Antennaefor Transfer of Magnetization to Bulk Water", Angewandte Chemie Int. Ed., 2002, vol. 41, No. 11, pp. 1919-1921, Wiley-VCH Verlag GmbH, Weinheim Germany.

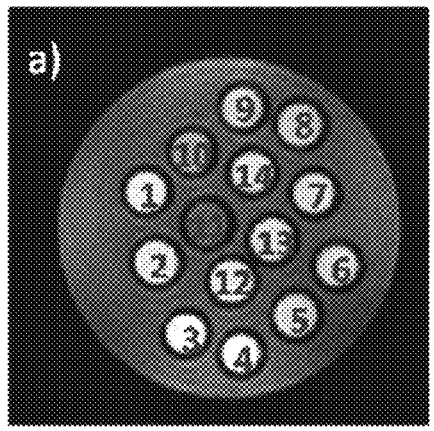
FIG. 3A
b)
1. 24mM pH=5.19    8. 24mM pH=7.59
2. 24mM pH=5.81    9. 24mM pH=7.91
3. 24mM pH=6.11    10. 24mM pH=8.27
4. 24mM pH=6.42    11. 24mM pH=8.75
5. 24mM pH=6.67    12. 12mM pH=7.31
6. 24mM pH=7.04    13. 6mM pH=7.31
7. 24mM pH=7.31    14. 3mM pH=7.31
FIG. 3B
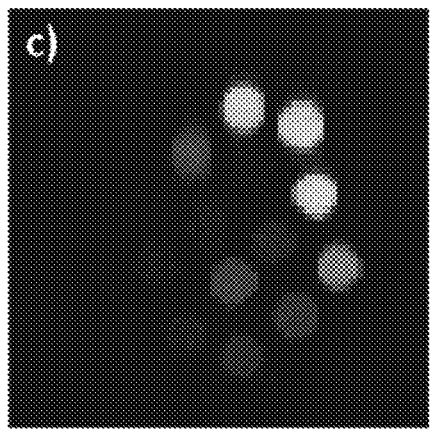
FIG. 3C
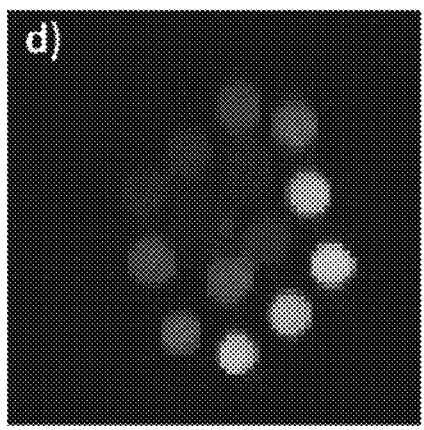
FIG. 3D Cell pellets legend
1. blank
2. Pinocytosis 37° C
3. Electroporation
4. Empty capillary 1. 8.4 mM
2. 4.2 mM
3. 2.1 mM
4. 1.05 mM
5. 0.52 mM
6. 0.26 mM

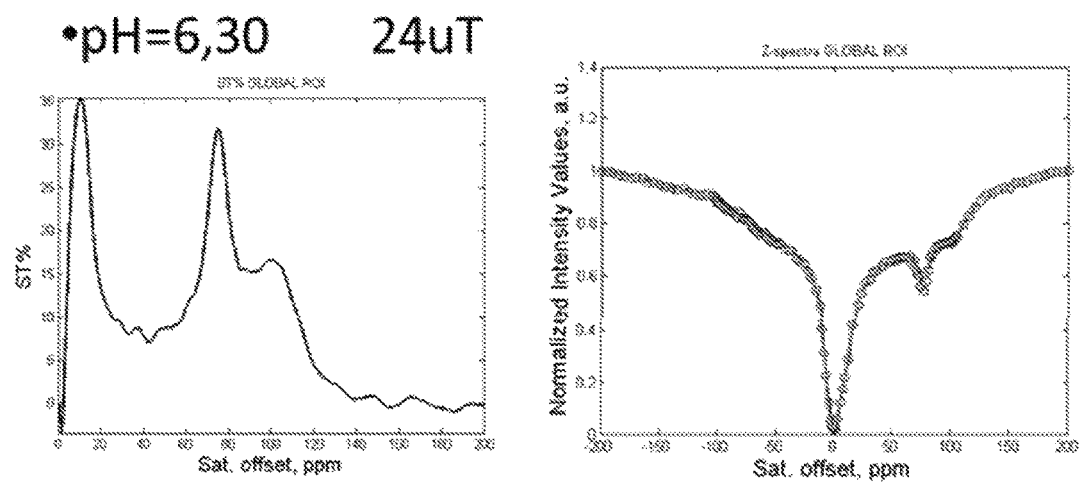
Figure 20
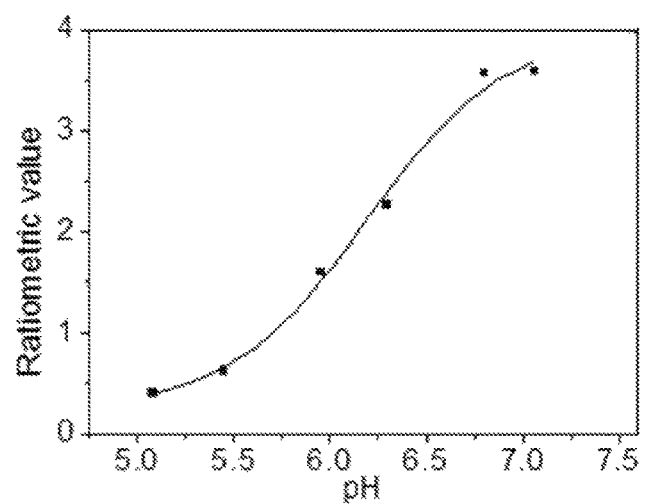

CEST SYSTEMS EXHIBITING A CONCENTRATION INDEPENDENT RESPONSIVENESS

FIELD OF THE INVENTION

The present invention relates to the field of Magnetic Resonance Imaging (MRI) based on Chemical Exchange-dependent Saturation Transfer (CEST), More in particular, it relates to CEST systems exhibiting a concentration independent responsiveness and to their use in in vivo mapping of physical or chemical parameters of diagnostic interest.

STATE OF THE ART

Chemical Exchange Saturation Transfer (CEST) modality is a recently introduced imaging procedure based on the use of molecules (CEST agents) containing one or more exchangeable proton(s) pools (see, for instance, Balaban R S., Methods in Biomedical Magnetic Resonance Imaging and Spectroscopy, Chichester, UK: John Wiley & Sons; 2000. Vol. 1. p 661-6667; Young I R, editor).

This imaging technique relies upon a phenomenon, known in high resolution NMR as double resonance experiment, in which a second radio frequency (rf) pulse is applied, finely centred at the resonance frequency of the mobile protons, derivable from the NMR spectrum, to saturate thereof spins. A saturated magnetization is thus created that is, transferred to the "bulk" water by chemical exchange, resulting in a neat reduction of the bulk water signal. This effect is referred to as Saturation Transfer or ST effect. The contrast in the resulting CEST based MR image is determined by the extent of the transfer: the larger is the amount of the saturated magnetization transferred to water protons, the smaller is the resulting water signal's intensity, the stronger is the contrast (negative contrast) in the recorded MRI image.

Basic requisite for a CEST agent is the presence of mobile proton(s) (or exchangeable protons, as herein used interchangeably) having appropriate exchange rate ($K_{ex}$), and suitable chemical shift separation with bulk water protons so that to allow both exchanging site activation and transfer of the saturation. Roughly, this condition is reached when $k_{ex}$ approaches ($K_{ex} \cong \Delta\nu$) where $\Delta\nu$ is the chemical shift separation in Hz between the two exchanging pools. Known CEST contrast agents are mainly grouped in diamagnetic and paramagnetic systems. Suitable examples of low molecular weight diamagnetic CEST agents (DIACEST) were first provided by Balaban in WO 00/66180, who carried out most of the work in this field. Macromolecular diamagnetic agents are, instead, disclosed, for instance, in J. Am. Chem. Soc 2001; 123:8628-8629.

Paramagnetic CEST agents (PARACEST), mainly including macrocyclic tetr-aamide derivatives of DOTA providing for four magnetically equivalent, or pseudo-equivalent, N-H mobile protons pools, where first reported by Sherry (see, for instance, J. Am. Chem. Soc 2001; 123:1517-1518). Important findings on paramagnetic CEST agents are also discussed in Magn. Reson. Med 2002; 47:639-648.

Woods et. al demonstrated that also OH groups can be exploited in a CEST experiment with a PARACEST probe, at least under certain experimental conditions, including the use of dry solvents (see, for instance, J. Am. Chem. Soc 2006; 128:10155-10162). However, by dissolving the tested complex in pure water, no CEST effect could be detected from hydroxyl and metal bound water protons, thus preventing its possible use for "in vivo" CEST applications.

Later on, Morrow and co-workers demonstrated that CEST effect from alcohols donor groups can be detected its pure water, by using three-positively charged Ln(III) macrocyclic complexes with neutral ligands comprising pendant alcohol groups (see, for instance, Inorg. Chem. 2009; 48:7237-7243). The existence of multiple stereoisomers of the used cyclen derivatives is discussed in the article which concludes that Ln(III) complexes having just one diastereomeric form in solution are potentially advantageous for PARACEST experiments.

An additional class of particularly high sensitive paramagnetic CEST agents is represented by LIPOCEST, liposomes containing a paramagnetic shift reagent for water protons in the aqueous inner cavity (see, for instance, Angew. Chem. Int Ed Engl 2003; 42:4527-4529).

Among CEST agents, a class of particular interest is represented by "responsive" agents, namely contrast agents endowed with at least one exchangeable proton whose saturation transfer capability correlates to a physico-chemical parameter of diagnostic interest of the microenvironment in which the agent distributes. These agents, beside acting as typical CEST agents and providing CEST contrast, are also able to report about changes of the said parameter, typically selected from pH, temperature, metabolites or specific ions concentration, $O_2$ or $CO_2$ partial pressure, proteins or enzymes activity, in the body organ or region in which they distribute, thus acting as useful biomarkers of specific disease strictly related to these changes (see, for instance, Top Curr. Chem 2002, 221, 123-164).

To this extent, the amount of saturation transfer (ST) observed in a CEST procedure depends on the water and CEST probe contents, i.e., in other words, its local concentration in the concerned tissue. By consequence, the peculiar responsive property exhibited by these agents may, in practice, be properly exploited only when thereof actual concentration is known.

Instead, to be effectively exploitable in in vivo determinations, a CEST responsive agent should display its responsiveness in a concentration independent mode.

This task can be achieved by using CEST agents containing at least two sets of magnetically non-equivaient protons whose ST effect shows a different dependence from the physicochemical parameter of interest.

In this case, in fact, a ratiometric approach may be exploited, based on the following equation (1)

$$\frac{[(M_0 - M_s)/M_s]_{site\ 1}}{[(M_0 - M_s)/M_s]_{site\ 2}} \quad (1)$$

pioneered disclosed by Balaban and Ward (for any detail on the above equation see, for instance, Magn. Reson. med., 2000; 44:799-802), exploiting a comparative ratio between the ST effects induced by the selective irradiation of the two different resonances, respectively identified as site 1 and site 2 in the above equation, that makes the measured ST amount and, in turn, the assessed diagnostic parameter, independent on the absolute concentration of the administered CEST probe.

Examples of responsive agents allowing the exploitation of this ratiometric approach include monomolecular lanthanide (Ln) complexes containing two magnetically non-equivalent proton sites, commonly belonging the one to primary amide group(s) on pendant arm(s) coordinated to the metal ion, wherein the second is typically represented by the water molecule(s) coordinated to the Ln centre of the chelated complex (see, for instance, Angew. Chem. Int Ed 2002; 41:1919-1921 and 4334-4336).

Diamagnetic molecules such as 5,6-dihydrouracil and iopamidol containing two pools of CEST-active protons have also successfully been experienced as concentration independent pH reporters (see, for instance, Magn. Reson. Med. 2000; 44:799-802, Invest. Radiol. 2004; 39:235-243; Magn. Reson. Med. 2005; 53:830-834 and J. Am. Chem. Sac 2005; 131:1380-1381).

Alternatively, CEST systems may be exploited comprising two (or more) CEST probes having the same biodistribution pattern but very different NMR, properties, for instance depending on the coordinated Ln(III) ion, each of which providing for a different proton pool(s) (see, for instance, Magn. Reson. Med. 2002; 47:639-648).

The development of responsive CEST agents is, however, still unsatisfactory, mainly because of the limited number of CEST systems exhibiting a concentration-independent responsiveness.

SUMMARY OF THE INVENTION

In accordance with the above task, the present invention is directed to the identification of an alternative source of magnetically non-equivalent mobile protons consenting to set-up CEST-based concentration independent responsive procedures and to alternative CEST systems exhibiting a concentration-independent responsiveness.

The solution of the present invention concerns using NMR-distinguishable steroisomers of a paramagnetic CEST agent as an alternative source of magnetically non-equivalent exchangeable protons.

More particularly, the present invention relates to the use of NMR-distinguishable isomers of a paramagnetic CEST agent as a source of magnetically non equivalent mobile protons to set a ratiometric-based CEST imaging procedure In a further embodiment the invention relates to a ratiometric-based CEST MRI procedure that comprises exploiting magnetically non-equivalent mobile protons belonging to at least two NMR-distinguishable isomers of a paramagnetic CEST aoent.

In a different embodiment theinvention relates to a class of Lanthanide (III) complex compounds endowed with a proton-exchanging group on a pendant arm of the chelating ligand that display at least two NMR distinguishable steroisomers in solution and to the use of these complex compounds in a ratiometric-based CEST imaging procedures as concentration independent CEST contrast agents to provide a concentration independent CEST contrast.

In a still further embodiment the invention relates to the use of the said identified Lanthanide (III) complex compounds as concentration-independent responsive CEST agents, and to a ratiometric-based CEST imaging method that comprises using thereof to provide concentration is independent maps of physical or chemical parameter of diagnostic interest in a human or animal body organ, fluid or tissue.

BRIEF DESCRIPTION OF THE DRAWINGS

FIG. 3A: In vitro MR image (proton density) of a phantom containing solutions of YbHPDO3A all having 24 mM concentration but different pH (capillaries 1-11), or same pH (7.31) but different concentrations (from 3 to 24 mM) (capillaries 7, 12-14).

FIG. 3B: Phantom legend.

FIG. 3C: ST map obtained upon irradiation of the hydroxilic protons at 72 ppm (20° C.; irradiation power pulse 24 µT).

FIG. 3D: ST map obtained upon irradiation of the hydroxilic protons at 99 ppm (20° C., irradiation power pulse 24 µT).

FIG. 20: ratiometric ST curve showing the dependence from pH of ratiometric values calculated, for the Compound 4, from ST curves obtained upon irradiation of hydroxylic protons at 75 and 100 ppm, respectively.

DETAILED DESCRIPTION OF THE INVENTION

Figure 1:
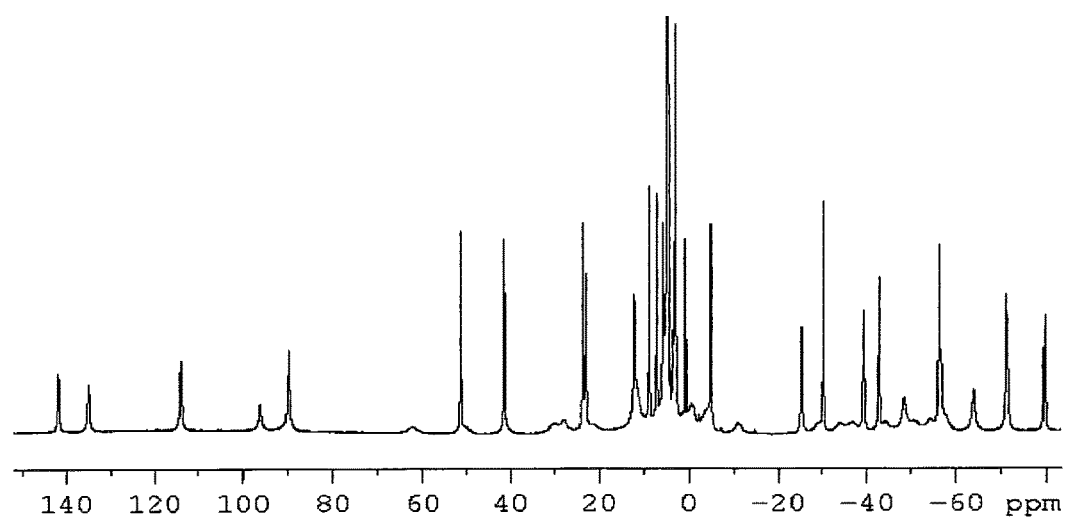
FIG. 1: $^1$H NMR Spectrum of YbHPDO3A in $D_2O$ (278 K, 600 MHz).

A source of magnetically non-equivalent mobile protons allowing to set-up a concentration-independent CEST MRI procedure, herein disclosed, is represented by the mobile protons belonging to at least two NMR-distinguishable isomers of a paramagnetic CEST agent.

In this respect, unless otherwise provided, the expression "NMR-distinguishable isomers of a CEST agent" refers to steroisomers of the CEST agent providing for mobile proton signals which are separated and, thus, distinguishable in the NMR spectrum, or, in other words, which show distinct resonances (in the NMR spectrum) for the exchangeable protons, each resonance corresponding to one of the NMR-distinguishable steroisomer.

To this extent, suitable CEST agents, providing for this kind of magnetically non-equivalent protons, are, preferably, Lanthanide (III) complex compounds comprising a proton-exchanging group on a chelating ligand pendant arm that display at least two NMR-distinguishable steroisomers in solution.

The NMR spectrum of these complex compounds, in fact, interestingly shows at least two separated resonances for the exchangeable proton, each corresponding to one of the NMR-distinguishable isomers, that may be selectively irradiated in ratiometric-based CEST imaging procedures.

The use of NMR-distinguishable isomers of suitable Lanthanide (III) complex compounds as a source of magnetically non equivalent mobile protons exploitable in a ratiometric-based CEST imaging procedure constitutes an embodiment of the instant invention.

It is now clear that, to properly exploit this alternative source of non-equivalent mobile protons in in-vivo CEST-based procedures, it is necessary that the lanthanide complex used as CEST probe displays a plurality of NMR distinguishable steroisomers under physiological conditions, or, in other words, that the resonances of the exchangeable protons of the different steroisomers displayed by the Ln(III) complex are still suitably shifted and well detectable in aqueous solution, at room temperature and physiological pH.

A particular class of Ln(III) complex compounds is herein identified, comprising a macrocyclic chelating ligand endowed with an hydroxyl (—OH) proton-exchanging group on a pendant arm, that exists in solution as a mixture of a plurality of NMR distinguishable isomers. Advantageously, the NMR spectrum of these complex compounds displays at least two resonances for the exchangeable OH protons, corresponding to different steroisomers, that are still present and well separated in aqueous solution, and under physiological pH and temperature conditions.

The use of this particular class of lanthanide (III) complex compounds in a ratiometric-based CEST imaging procedure represents a preferred embodiment of the instant invention.

Therefore in one embodiment the present invention relates to the use of lanthanide (III) complex compounds comprising a chelating ligand endowed with a hydroxyl proton exchanging group on a pendant arm in ratiometric-based CEST imaging procedures that exploit (at least two) magnetically non-equivalent mobile protons each provided by a NMR distinguishable steroisomer of the concerned lanthanide complex.

Suitable Lanthanide (III) metal ions (or Ln(III)) are selected from the group consisting of: praseodymium (III), neodymium (III), dysprosium (III), erbium (III), terbium (III), holmium (III), thulium (III), ytterbium (III), and europium (III), where europium (III) and ytterbium (III) are preferred and ytterbium (III) is particularly preferred.

On the other side, suitable chelating ligands according to the invention include macrocyclic chelating ligands endowed with a hydroxyl (OH) proton exchanging group on a single pendant arm.

Preferred are chelating ligands of formula (I)

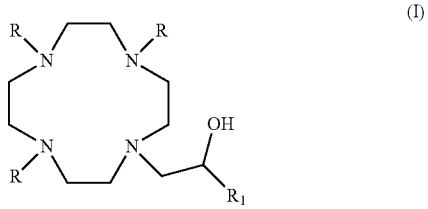

where
is —CH(R$_2$)—COOH,
R$_1$ is H or a straight or branched C$_1$-C$_5$ alkyl chain, that is optionally interrupted by a group selected from —O—, —N—, —CO—, —NHCO—, —CONH— group, and optionally substituted by one or more halogen atoms, hydroxyl (—OH) groups, a phenyl or a substituted phenyl group, or by a group selected from —COOH, —NHR$_3$ or —NR$_4$R$_5$, wherein R$_3$, R$_4$ and R$_5$ are, the same or different from each other, H or a straight or branched C$_1$-C$_3$ alkyl group which is optionally substituted by one or more hydroxyl or C$_1$-C$_3$ alkoxy groups,
R$_2$ is H or a C$_1$-C$_5$ alkyl chain that is optionally substituted by one or C$_1$-C$_3$ alkoxy, or hydroxyalkoxy groups.

To this extent it should be clear to a skilled practitioner that, when the chelating ligand of formula (I) is complexed with a three-positively charged Lanthanide (III) metal ion, the carboxylic group of the moiety R is in the corresponding deprotonated (—CH(R$_2$)—COO$^-$) form.

In the present description, unless otherwise provided, with the term straight or branched C$_1$-C$_5$ alkyl group we intend a linear or branched alkyl chain with from 1 to 5 carbon atoms. Suitable examples for alkyl groups comprise methyl, ethyl, n-propyl, isopropyl, n-butyl, isobutyl, sec-butyl, tert-butyl, n-pentyl, and the like.

The above alkyl groups may be further substituted and/or interrupted by one or more halogen, hydroxyl, alkoxy, amino, hydroxyalkoxy, phenyl or substituted phenyl group as set forth above.

With halogen or halogen atoms we intend a iodine, chlorine, bromine, or fluorine atoms, these latter being particularly preferred.

With the term substituted phenyl, we intend a phenyl group the is substituted by one or more halogen atom, hydroxyl (OH), or C$_3$-C$_3$ alkoxy groups, or a group selected from —(CH$_2$)$_n$COOH, —NO$_2$, —NHR$_3$, or a —NR$_4$R$_5$ is group, in which n is 0 or 1 and R$_3$, R$_4$, and R$_5$ are as defined above.

With the term C$_1$-C$_3$ alkoxy we intend any alkyl-oxy group wherein the alkyl moiety include up to 3 carbon atoms.

With hydroxyalkcixy group we intend any the above C$_1$-C$_3$ alkoxy groups wherein the alkyl moiety is further substituted by an hydroxyl group.

Suitable examples of alkoxy or hydroxyalkoxy groups of the invention comprise, for instance, methoxy, ethoxy, n-propoxy, hydroxymethyloxy, —2-hydroxyethoxy, 2,3-dihydroxypropoxy, and the like.

Preferably, within the compounds of formula (I) R$_2$ represent H, and R$_1$ is H or a straight or branched C$_1$-C$_4$ alkyl chain, optionally interrupted by an oxygen atom, or substituted by a —OH, —NH$_2$ or a phenyl group that may be in its turn substituted or not by an hydroxyl, a C$_1$-C$_3$ alkoxy, a nitro or a carboxyl group.

Even more preferably, within the core pounds of formula (I) R$_2$ is H and R$_1$ represents a group selected from:
—H,
—CH$_1$,
—CH$_2$CH$_3$,
—CH$_2$OH,
—CH$_2$—O—CH$_3$,
—CH(CH$_2$OH)$_2$,
—CH$_2$—CH(OH)—CH$_2$OH,
—CH$_2$—O—CH$_2$—C$_6$H$_5$,
—CH$_2$—O—CH$_2$—(C$_6$H$_5$—COOH),
—CH$_2$—O—CH$_2$—(C$_6$H$_5$—NO$_2$).

Especially preferred according to the invention is a Ln(III) complex of a ligand of formula (I) in which in which R$_2$ is H and R$_1$ is —CH$_3$, while the chelated Ln (III) ion is selected from Yb(III) or Eu(III).

Dimer or multimer derivatives comprising at least two chelating ligand of formula (I), optionally linked through their R$_1$ groups that may be suitably functionalized, if appropriated, are comprised within the present invention, and are generally endowed with an increased sensitivity.

Accordingly, in a different embodiment the invention relates to Ln(III) complex compounds wherein the chelating ligand is a dimeric or multimeric derivative of a compound of formula (I).

One example of this type of compound is, for instance, disclosed in Example 1 below, together with the scheme for its preparation.

The tetrameric chelating ligand of Example 1, or HPDO3A-Tetramer, as used herein interchangeably, as well as the salts thereof and the chelated complexes thereof with (up to) four paramagnetic metal ions are novel and constitute a further object of the present invention.

To this extent, suitable paramagnetic metal ions within are selected from the following: Fe($^{2+}$), Fe($^{3+}$), Cu($^{2+}$), Ni($^{2+}$), Rh($^{2+}$), Co($^{2+}$), Cr($^{3+}$), Gd($^{3+}$), Eu($^{3+}$), Dy($^{3+}$), Tb($^{3+}$), Pm($^{3+}$), Nd($^{3+}$), Tm($^{3+}$), Ce($^{3+}$), Y($^{3+}$), Ho($^{3+}$), Er($^{3+}$), La($^{3+}$), Yb($^{3+}$), Mn($^{3+}$), Mn($^{2+}$). More preferably, the paramagnetic metal ion is Gd($^{3+}$) or a lanthanide metal selected from Yb($^{3+}$), Eu($^{3+}$) or Dy($^{3+}$).

Figure 9:
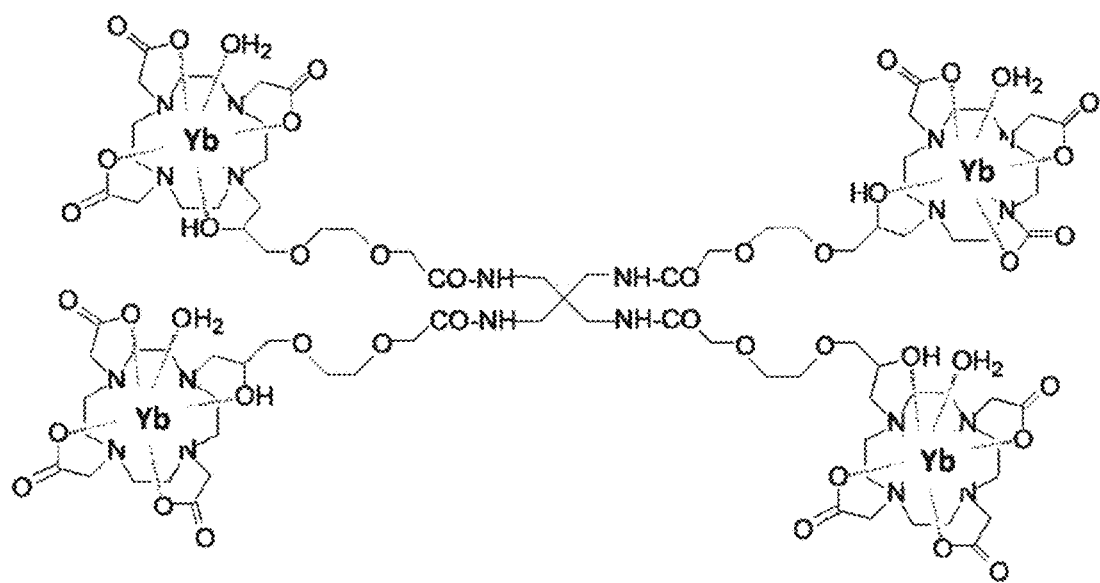
FIG. 9: Formula of the tetrameric derivative of the YbHPDO3A, otherwise identified as $(Yb^{3+})_4$HPDO3A-tetramer or, simply, Tetramer.

An additional object of the present invention is a diagnostic composition comprising a paramagnetic or, especially, a Ln(III) bis- or poly-chelated complex of a dimeric or a multimeric derivative of a chelating ligand of formula (I), or a physiologically acceptable salt thereof, together with suitable additives and/or carriers for use in the MR Imaging. In a preferred embodiment, the said diagnostic composition comprises (Yb$^{3+}$)$_4$HPDO3A-Tetramer, having the structure of FIG. 9.

The chelating ligand of formula (I), comprising at least three carboxylic groups on a macrocyclic skeleton, can conveniently be in the form of physiologically acceptable salts.

Suitable examples of cations of inorganic bases that can be used to salify the ligands of the invention comprise ions of alkali or alkaline-earth metals such as potassium, sodium, caicium or magnesium.

Preferred cations of organic bases comprise, inter alia, those of primary, secondary and tertiary amines such as, ethanolamine, diethanolamine, morpholine, glucamine, N-methylglucamine, N,N-dimethylglucamine.

Preferred anions of inorganic acids that can be suitably used for this purpose comprise the ions of halo acids such as chlorides, bromides, iodides or other ions such as sulfate.

Preferred anions of organic acids comprise those of the acids routinely used in pharmaceutical techniques for the salification of basic substances such as, for instance, acetate, succinate, citrate, fumarate, maleate or oxalate.

Preferred cations and anions of amino acids comprise, for example, those of taurine, glycine, lysine, arginine ornithine or of aspartic and glutamic acids.

On the other side, the three carboxylic group of the macrocyclic ligand are all involved with the chelation of a three-positively charged lanthanide ion. As a result, the Ln(III) complex compounds of formula (I) are neutral, and thus suitable for in vivo applications without any further neutralization or salification.

In case, instead, the chelating ligand comprises a further acidic group on its structure, its neutralization with a cation routinely used in pharmaceutical techniques, for instance selected from those listed above, is necessary to provide a physiological acceptable salt thereof.

The Ln(III) chelated complexes of formula (I) in which $R_1$ is different from H, and the dimer or multimer derivative thereof, include a chiral centre, represented by the hydroxylated carbon on the pendant arm. Therefor, in solution, they display a plurality of steroisomeric forms differing, essentially, in the layout of the acetate arms (clockwise or counterclockwise oriented), in the two conformation of the macrocyclic ring and in the conformation of chiral centre (R,S), To this extent a skilled person is aware that when $R_1$ is H, the said carbon looses its chirality, but the isomers differing in the layout of the acetate arms or in the conformation of the ring still exist.

The present invention is based on the observation that the diasteroisomers displayed in aqueous solution, at room temperature, by this preferred class of complex compounds are distinguishable in the NMR spectrum. More particularly, we have found that the Ln(III) complex compounds of formula (I), set forth by the invention, display in solution, at physiological temperature and pH, at least two suitably shifted resonances for the exchangeable OH protons, each corresponding to a different, NMR-distinguishable, diasteroisomer of the complex. Advantageously, the different steroisomers of the same complex have proven to have the same in vivo biodistribution and same relative concentration ratio over time. Therefore, the plurality of suitably shifted OH proton resonances the NMR-distinguishable steroisomers of a Ln(III) complex compound of formula (I) display in solution may profitably be used to set-up a ratiometric-based CEST-MRI procedure exploitable in in vivo conditions, to provide in vivo CEST images that are unaffected by the local concentration of the concerned complex.

Moreover, interestingly, the amount of saturation transfer ST obtained by selective saturation of the OH exchangeable protons of the Ln(III) complex compounds according to the invention is markedly sensitive to, or, in other words, responsive for physical or chemical parameters of the microenvironment in which they distribute. As a result, the particular class of Ln(III) complex compounds set forth by the present invention, beside being exploitable in CEST imaging procedure to provide concentration-independent CEST contrast, may also profitably be exploited as responsive CEST agents, particularly in rationietric-based CEST imaging procedures allowing to provide in vivo measures and maps of physical or chemical parameters of diagnostic interest that are not affected by the local concentration of the agent itself.

Accordingly, in a further embodiment, the instant invention relates to the use of a Ln(III) complex compound of formula (I) as concentration independent CEST responsive agent, especially in ratiometric-based CEST imaging procedure for the in viva determination of physical or chemical parameters of diagnostic interest.

In the present invention, unless otherwise indicated, with physical or chemical parameter of diagnostic interest we intend a parameter selected from temperature, pH, partial pressure of oxygen ($pO_2$) or carbon dioxide ($pCO_2$), specific ion or metabolite concentration, or specific enzymatic activity.

To this extent it is now clear that, by knowing, the value, or the map, of physical or chemical parameter(s) in the body organ or region under investigation, a physician may provide diagnostic evaluations of those physiological or metabolic process of diagnostic interest that strictly rely on the said assessed parameter(s).

In a still further embodiment the invention relates to a ratiometric-based CEST MRI procedure that comprises exploiting, i.e. irradiating with a suitable radio-frequency pulse and, thus, inducing a saturation transfer to the bulk water signal, at least two magnetically non-equivalent mobile protons that are provided by two or more NMR-distiguishable steroisomers of a suitable CEST probe.

To this extent it should be clear to a skilled artisan that a ratiometric-based CEST MRI procedure exploiting magnetically non-equivalent mobile protons belonging to NMR-distinguishable isomers of any suitable CEST probe is comprised within the present invention. In a preferred embodiment, the concerned CEST probe is a paramagnetic CEST agent and, more preferably, is a Ln(III) complex compound set forth by the present invention.

In an particularly preferred embodiment, the CEST probe is a Ln(III) complex of the HPDO3A chelating ligand, or a bis- or poly-chelated complex of its dimeric or a multimeric derivative, or a physiologically acceptable salt thereof.

Accordingly, in a preferred embodiment thereof, the instant invention relates to a ratiometric-based CEST MRI procedure that comprises using a Ln(III) complex compound of formula (I), or a dimer or multimer derivative thereof, to provide concentration independent in viva CEST imaging. Even more preferably, the said ratiometric-based CEST MRI procedure is employed for the in vivo determination of physical or chemical parameter of diagnostic interest in a human or animal body organ, fluid or tissue that is unaffected by the local concentration of the CEST agent.

More particularly, in a preferred embodiment the invention relates to a concentration-independent CEST Imaging procedure for obtaining images of a human or animal body organ, region, fluid or tissue, that comprise:
  a) administering a Ln(III) chelated complexes of formula (I) or a dimer or multimer derivative thereof to a human or animal subject and, optionally, recording MRI morphological images of the human or animal body organ region, fluid or tissue of interest, preferably by using $T_2$ weighted sequences,
  b) collecting a Z spectrum in a range of frequencies finely tuned on the resonance frequencies of two magnetically non equivalent mobile protons belonging to NMR-distinguishable steroisomers of the administered Lanthanide complex, and calculating the ratiometric values from the saturation transfer effect (ST) measured for these two mobile protons pools,
  c) obtaining concentration independent images of the said human or animal body organ region, fluid or tissue,
wherein the step C of the procedure preferably comprises superimposing he ratiometric values map, obtained from measured ST effects in step b) of the procedure, on previously recorded morphological images of the concerned human or animal body organ, region, fluid or tissue. To this extent, in step b) the resonance frequencies of the two magnetically non equivalent mobile protons is obtained from the NMR spectrum of the complex, that, if not already known, can be suitably recorded before CEST imaging.

The above CEST Imaging procedure can be implemented in vitro (ex vivo) or, preferably, in vivo, for obtaining in vivo images of a human or animal body organ, region, fluid or tissue.

In another preferred embodiment the invention relates to a method for determining, by use of the CEST MRI technique, a physical or chemical parameter of diagnostic interest in a human or anima body organ, region, fluid or tissue that comprise:

administering a Ln(III) chelated complexes of formula (I) or a dimer or multimer derivative thereof to a human or animal subject and, optionally, recording MRI morphological image of the human or animal body organ, region, fluid or tissue of interest, ii) collecting a Z spectrum, in a range of frequencies finely tuned on the resonance frequencies of two magnetically non equivalent mobile protons belonging to NMR-distinguishable steroisomers of the administered Lanthanide complex, and calculating the ratiometric values from the saturation transfer effect (ST) measured for these two mobile protons pools, iii) obtaining, from the calculated ST, a concentration independent map (or ratiometric map) of the parameter of interest in the concerned human or animal body organ, region, fluid or tissue and, optionally, superimposing the said map on the morphological image, the said determination being performed in vitro (ex vivo) or, preferably, in vivo, in a human or animal body organ, region, fluid or tissue.

In an especially preferred embodiment, the invention relates to a concentration-independent CEST Imaging procedure for obtaining in vivo maps of the pH in a human or animal body organ, region, fluid or tissue of interest that comprise exploiting two magnetically non equivalent mobile protons belonging to NMR-distinouishable steroisomers of a Ln(III) chelated complex of the HPDO3A chelating ligand, or of a dimer or multimer derivative thereof, or of a physiologically acceptable salt thereof.

To this extent, a skilled practitioner is aware that the imaging steps above detailed, including irradiating the mobile proton frequency, collecting the Z-spectrum, calculating a ratiometric ST effect and, by using calibration curves previously performed, obtaining a map of the desired physical or chemical parameter in a body organ or region, are automatically performed by the tomography, once properly set, in accordance with procedures used in the current diagnostic practice, and by using data processing procedures, for instance disclosed in the imaging protocol provided in the experimental section and in the cited literature, herein incorporated by reference.

In the methods of the invention, the Ln(III) complex compound of formula (I) (or the dimmer o multimer thereof, or a physiologically acceptable salt thereof) acting as CEST agent according to the invention is administered in the form of a suitable pharmaceutical preparation.

To this extent, according to a particularly preferred embodiment of the present invention both of the above CEST-based procedures are performed on human or animal bodies, suitably pre-administered with a pharmaceutical preparation comprising a suitable amount of the Lanthanide complex compound according to the invention. In other word, according to a particularly preferred embodiment, the instant invention relates to a method for the in vivo imaging of a human or animal body organ, region, fluid or tissue or for the in vivo assessment or mapping, by use of the CEST MRI technique, of a physical or chemical parameter of diagnostic interest in a human or animal body organ, region, fluid or tissue by use of the CEST-based Magnetic Resonance Imaging technique that is carried out on a human or animal body suitably pre-administered with a pharmaceutical preparation comprising a suitable amount of a Lanthanide (III) complex compound according to the invention. With "suitable amount", as used herein, we refers to any amount of a contrast agent, of the invention, or pharmaceutical composition thereof, that is sufficient to fulfil its intended diagnostic purpose(s); i.e., for example, to acquire concentration independent contrasted images or providing concentration independent maps of a parameter of interest in a concerned human or animal body organ, region, fluid or tissue, by use of CEST based MRI imaging technique.

In this respect, the said administration or pre-administration can, for instance, occurs by intravasal injection (for instance intravenous, intraarterial, intraventricular injection, and so on) or intrathecally, intraperitoneally, intralymphaticly, intracavitally, orally or enterally. Injectable pharmaceutical formulations of Lanthanide (III) complex compounds of formula (I) are typically prepared by dissolving the active ingredient, namely the lanthanide complex, or a pharmaceutically acceptable salt thereof, and the pharmaceutically acceptable excipients in water of suitable purity from the pharmacological point of view. The resulting formulation is suitably sterilised and can be use as such or it can alternatively be lyophilised and reconstituted before the use.

These formulations can be administered in concentrations depending on the diagnostic requirements, at a dose ranging from 0.01 to 0.5 mmol/kg body weight.

As formerly said, particularly preferred, according to the present invention, is a Ln(III) complex of a ligand of formula (I) where $R_2$ is H and $R_1$ is —$CH_3$, while the chelated Ln (III) ion is selected from Y(III) or Eu(III). The lanthanide complex compounds of this, ligand have thus been used as non limiting, representative, example of the present invention.

This ligand is known in the art with the name HPDO3A and the chelated complex thereof with $Gd^{3+}$ is the well known contrast agent used in is conventional MRI imaging, long time marketed as ProHance™. The very low toxicity and the excellent tolerability exhibited by this agent are known in the art since long time and make its use in CEST imaging procedures particularly advantageous and safe, even at doses this technique requires, of up to 10 times the dosage (0.1 mmol/Kg) typically used in conventional MRI.

The structure of Gd (III) and Yb(III) complexes of HPDO3A has been determined by means of x-ray (see, for instance Kumar, K.; Chang, C. A.; Francesconi, L. C.; Dischino, D. D.; Malley, M. F.; Gougoutas, J. Z.; Tweedle, M. F. Inorg. Chem. 1994, 33, 3567-75). In the cited article it is reported that, even starting from a racemic solution, the presence of an asymmetric unit including the chiral 2-hydroxypropyl group results in two independent complexes having a diasteromeric conformation differing in the relative conformation of the macrocycle, while all the coordinating arms of the two isolated complexes have the same orientation, i.e. are twisted in the same sense.

In solution, the Ln(III) complexes of the HPDO3A, hawin the following structure (in which the OH mobile proton is circled),

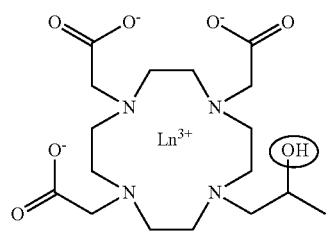 [SMILES: CC(O)CN1CCN(CC(=O)[O-])CCN(CC(=O)[O-])CCN(CC(=O)[O-])CC1]

typically display eight isomeric forms, more specifically four diasteroisomers and four enantiomers, that are schematized in the Scheme 1 below.

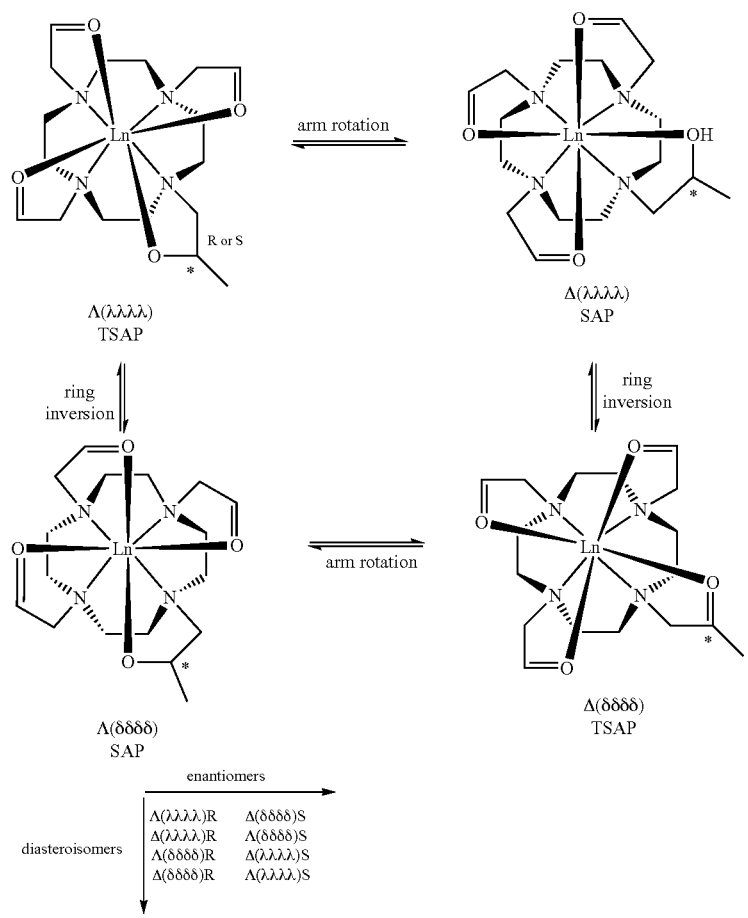

Two of the diasteroisomeric forms, most likely attributable to the form R and S, respectively, of the same conformer, are detectable in the NMR spectrum (shown in FIG. 1), and, particularly, in the Z-spectrum of Yb-HPDO3A (reported in FIG. 2b) that clearly shows two regions of saturation transfer, reasonably attributable to the two major diasteroisomers. An evidence of other two diasteroisomers may, instead, be derived by a comparison of the NMR spectra of the convlex recorded at different temperature.

Figure 2A:
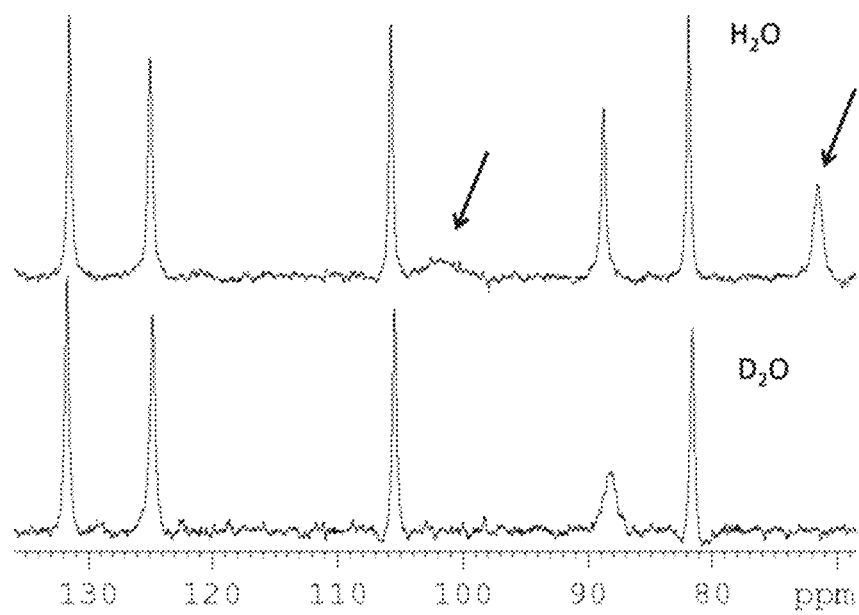
FIG. 2A: Magnification of the YbHPDO3A Spectrum in $D_2O$ (lower) and $H_2O$ (upper) in which the different chemical shifts (72 and 99 ppm, respectively, at 20° C.) exhibited by the exchanging OH protons of two distinguishable isomers of the complex are highlighted.
Figure 2B:
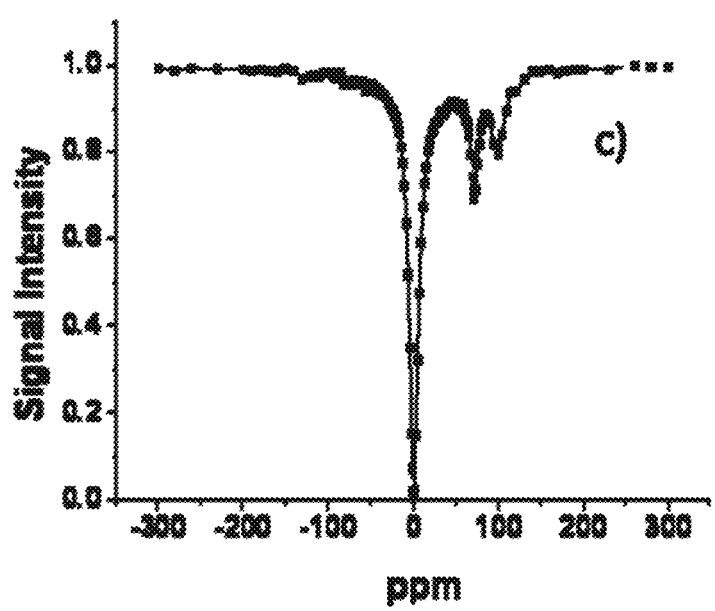
FIG. 2B: Z spectrum of YbHPDO3A (24 mM solution, 293 K, pH 7.31, irradiation power 24 µT, irradiation time 2 s).

In full agreement with all the above, the hydroxyl groups of two NMR-distinguishable diasteroisomers of the complex exhibit well different chemical shifts, respectively at 72 and 99 ppm at 20° C., shown in FIG. 2a), and different exchange rates, that may be exploited to set-up a ratiometric-based procedure according to the instant invention.

The responsiveness exhibited by this complex toward the pH has also been verified, by means of in vitro MRI experiments reported In details in the experimental section.

Obtained results confirm that the dependence of the saturation transfer on the pH displayed by each of the OH mobile protons of the Yb-HPDO3A diasteroisomers is different. This allows the exploitation of a ratiometric approach enabling a concentration-independent assessment of the intracellular pH in test performed with mesenchimal stem cells.

Figure 5A:
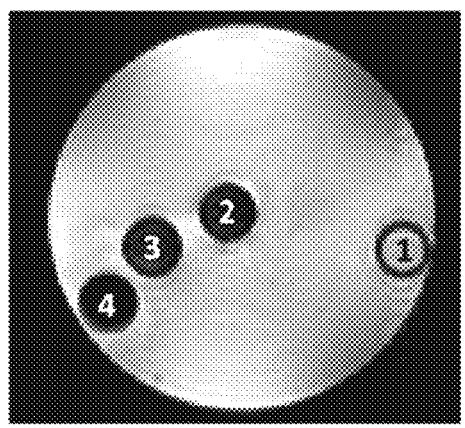
FIG. 5A: In vitro MR image of a phantom containing 3 different pellets of MSH cells that have been incubated (capillary 2) or electroporated (capillary 3) with a solution of YbHPDO3A, or cell incubated with PBS and used as reference (capillary 1). An empty capillary (4) is also included into the phantom.
Figure 5B:
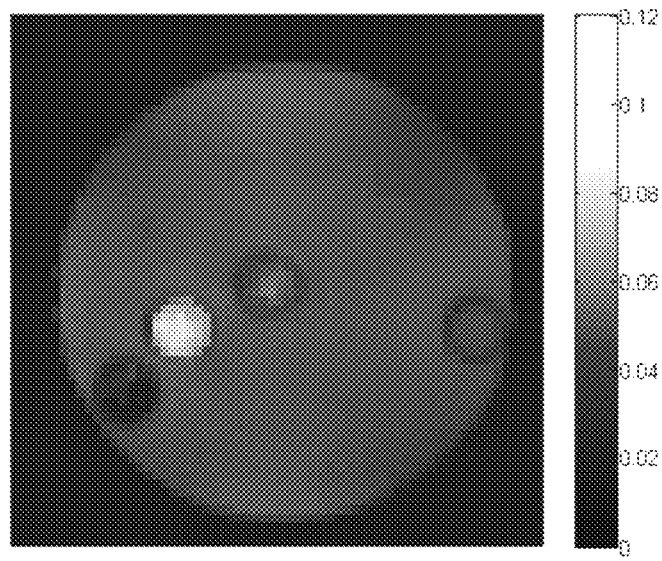
FIG. 5B: ST map collected upon irradiating the phantom at 72 ppm.
Figure 5C:
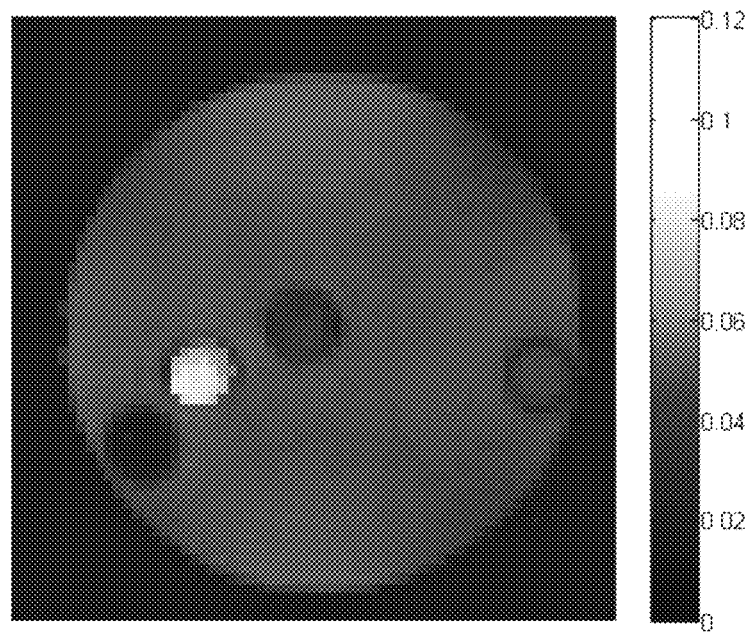
FIG. 5C: ST map collected upon irradiating the phantom at 99 ppm.

Interestingly, ST maps obtained from this test, shown in FIG. 5B and FIG. 5C, respectively, confirm that a ST effect could be seen only for those is cells incubated or electroporated with YbHPDO3A, while any saturation was recorded in absence of the complex. The observed ST effect was higher for those cells electroporated, corresponding to a measured pH of 7.00±0.2 while the pH measured in the pellet of cells 2 was 6.8±0.3

Figure 8:
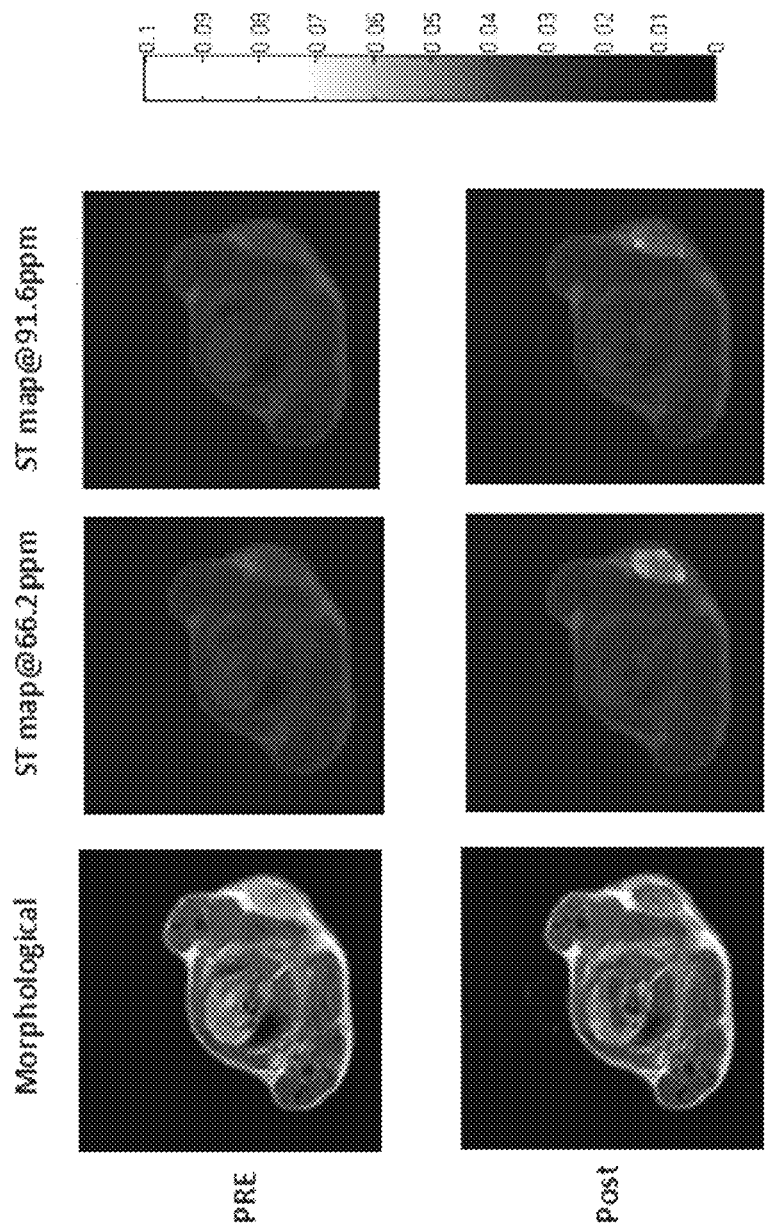
FIG. 8: morphological image (left images) and ST maps recorded in the tumor region of the mouse before (PRE), and immediately after (Post) i.v. injection of YbHPDO3A. The ST effect calculated upon irradiation at, respectively 66.2 and 91.6 ppm has been superimposed on the corresponding anatomical image where the tumor region appear lighter area (red in the image actually observed). In the figure, the symbol @ indicates the irradiation frequency used to promote the saturation transfer.

Notably, the high sensitivity exhibited by Yb(III) HPDO3A toward pH, allowed its effective use in the determination of the environmental pH in a tumor region (subcutaneous tumor), as shown in FIG. 8. This result, to our knowledge, had never been achieved before with CEST agents.

The responsiveness exhibited by Yb(III)HPDO3A toward environmental temperature has been also tested. Obtained results highlighted, in particular, the relevant sensitivity to the temperature displayed by the chemical shifts of the two hydroxylic protons of the two NMR-distinguishable disteromers. Thus, since the chemical shift doesn't depend on the concentration, the temperature of the environment may exactly be obtained simply by the value of the chemical shift observed in the Z-spectrum of the complex.

As expected, a greatly eased sensitivity, particularly toward temperature, has been observed with the tetrameric derivative of Yb(III)HPDO3A, including up to four OH mobile protons for each of the distinguishable steraisorners.

Figure 12A:
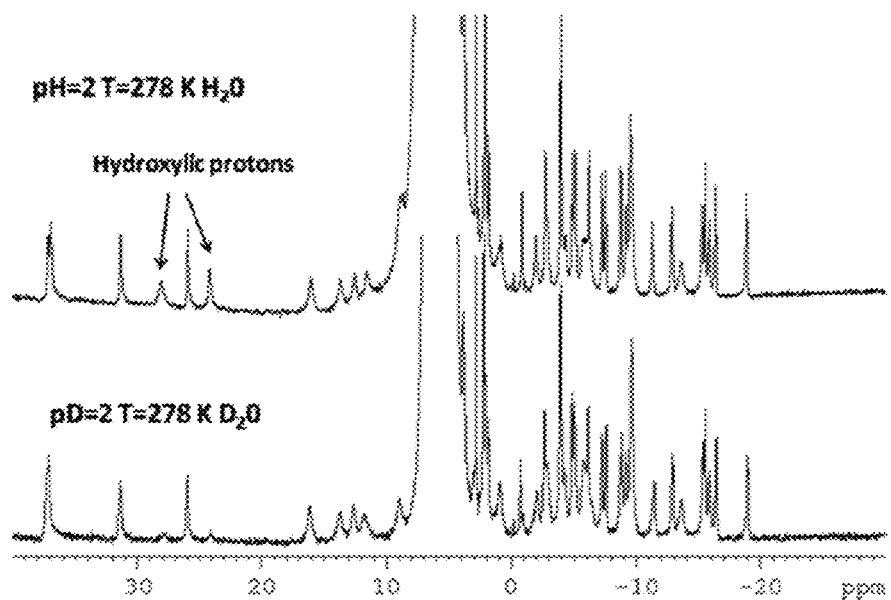
FIG. 12A: $^1$H NMR Spectrum of EuHPDO3A $D_2O$.
Figure 12B:
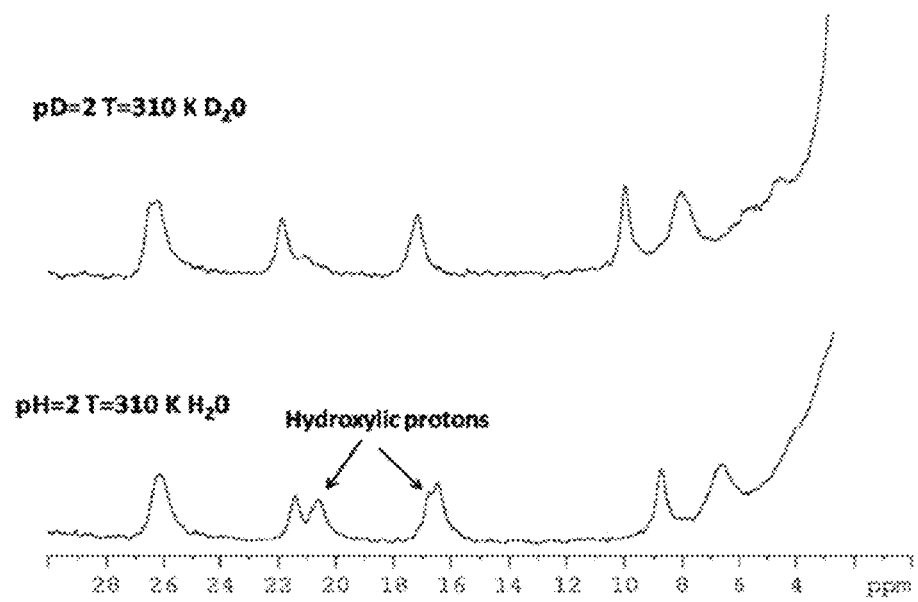
FIG. 12B: Magnification of the EuHPDO3A NMR Spectrum in $D_2O$, 278 K, pH 2 (upper) and $H_2O$, 310 K, pH 2 (lower) confirming the existence of two NMR distinguishable isomers, having chemical shift 20.5 and 16.7 respectively (pH2 and 20° C.), still distinguishable at physiological temperature (Advance 600 spectrometer).
Figure 13A:
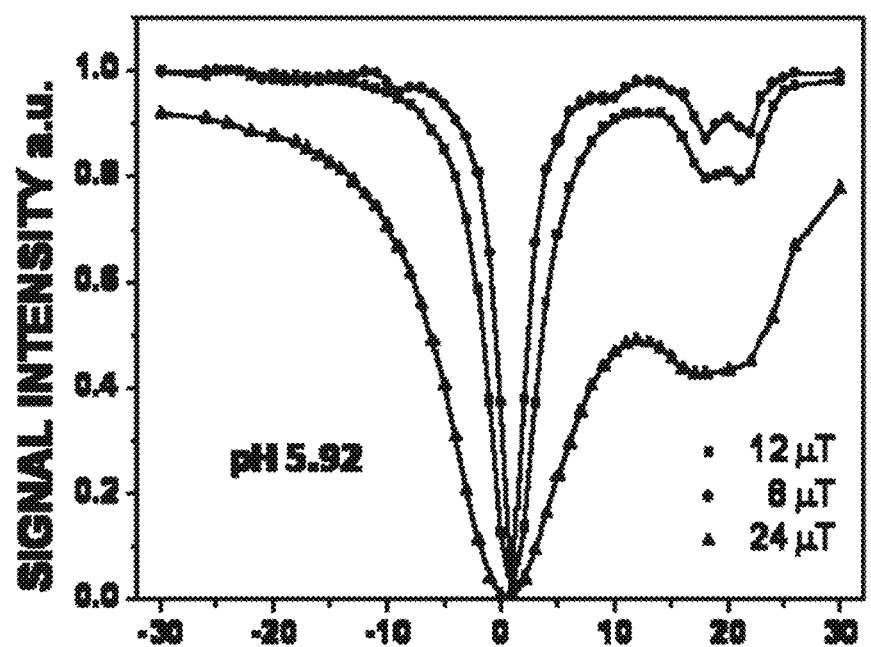
FIG. 13A: Z-spectra of EU(III)HPDO3A (20 mM) at pH 5.92 and 37° C. at different power pulse.
Figure 13B:
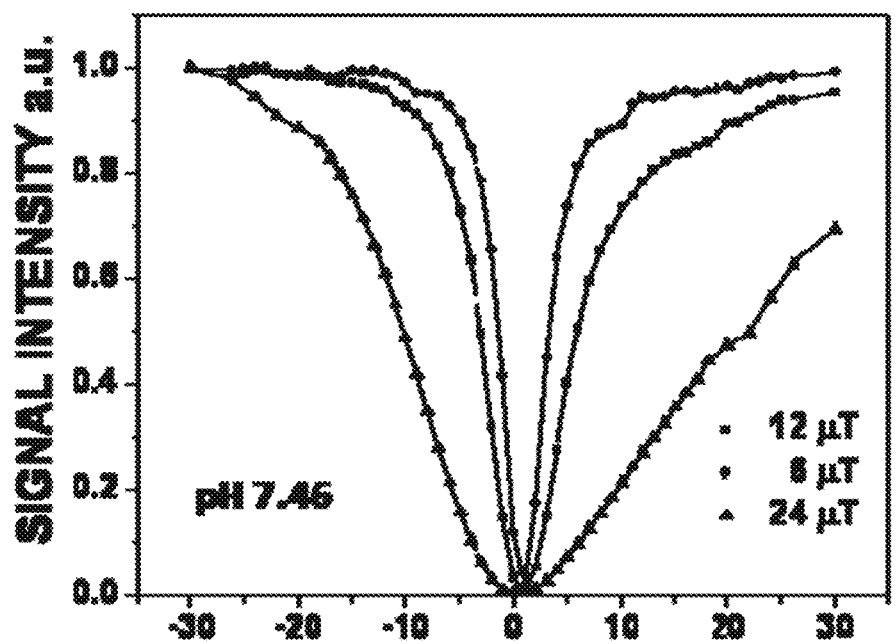
FIG. 13B: Z-spectra of EU(III)HPDO3A (20 mM) at pH 7.46 and 37° C. at different power pulse.
Figure 13C:
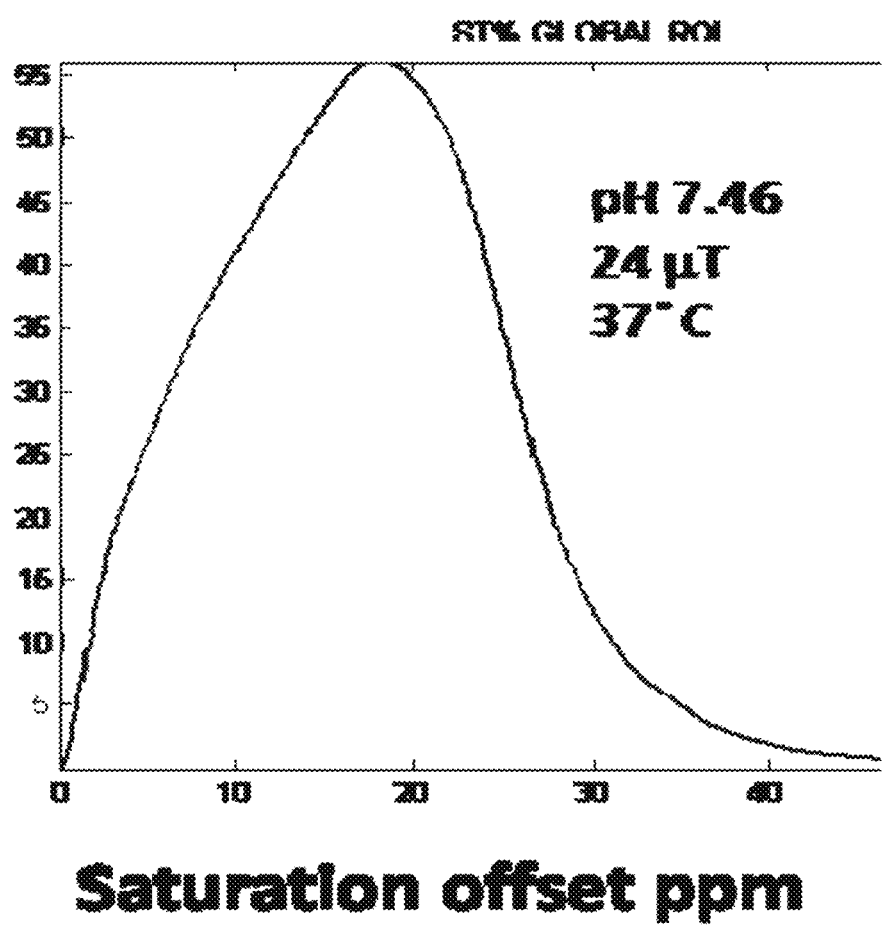
FIG. 13C: ST-profile of EU(III)HPDO3A 20 mM at pH 7.46, 37° C. and irradiation power of 24 µT.

The same re ponsiveness toward pH exhibited by Yb(III) HPDO3A was also proven for the corresponding Eu(III) complex compound. The NMR spectrum of this complex, shown in FIG. 12, clearly displays the presence of two major isomers. The signals belonging to the hydroxylic group of these isomers have been assigned by comparing the NMR spectra of two different solution containing EuHPDO3A in water and D$_2$O, respectively. Two chemical shifts (for the OH protons of the two diasteroisomers) have, thus, been assigned, respectively at 20.5 ppm (from water), and 16.7 ppm, at pH=2 and 37° C. However, as appears from FIG. 13, by increasing the solution pH towards physiological values, the proton exchange rate increases and the separation in chemical shift between these two signals decreases rendering difficult thereof selective irradiation under physiological conditions. A ST profile was, however, recorded by using different irradiation pulse, showing that by working at 6 μT (irradiation power) it is possible to observe both of the two distinct resonances and then perform a ratiometric measurement, while a saturation transfer is in any case still observable by using a resonance frequency of intermediate value (with respect to the real absorption frequencies), namely about 18 ppm.

From all the above it results that YbHPDO3A and EuHPDO3A may effectively be used as responsive CEST agents for the in vivo assessment of pH and temperature.

To this extent, one can safely assume that both of Yb- and Eu-HPDO3A have the same properties, in terms of biodistribution, excretion and tolerability, shown by ProHance®, the corresponding Gadolinium complex and they, accordingly, may enable the same kind of conventional anatomical imaging it promotes. Advantageously, however, the use of the Yb- and Eu-complexes allows the acquisition of CEST-based anatomical images and to further supplement and integrate the anatomical information already enabled by ProHance® in conventional MRI with additional information concerning pH and/or temperature of the said enhanced anatomical region wherein the agent distributes.

As a further proof of principle, the responsiveness to the pH displayed by the Yb(III) complex of the 4-[2-hydroxy-3-[4,7,10-tris[carboxymethyl 2-(1,1-dimethylethoxy)-1,4,7,10-tetraazacyclododec-1-yl]propoxy]benzoic acid (hereinafter Compound 2) having the following formula

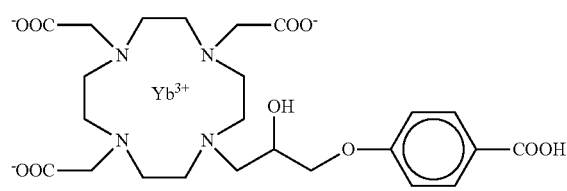

Compound 2 was also assessed.

Figure 14:
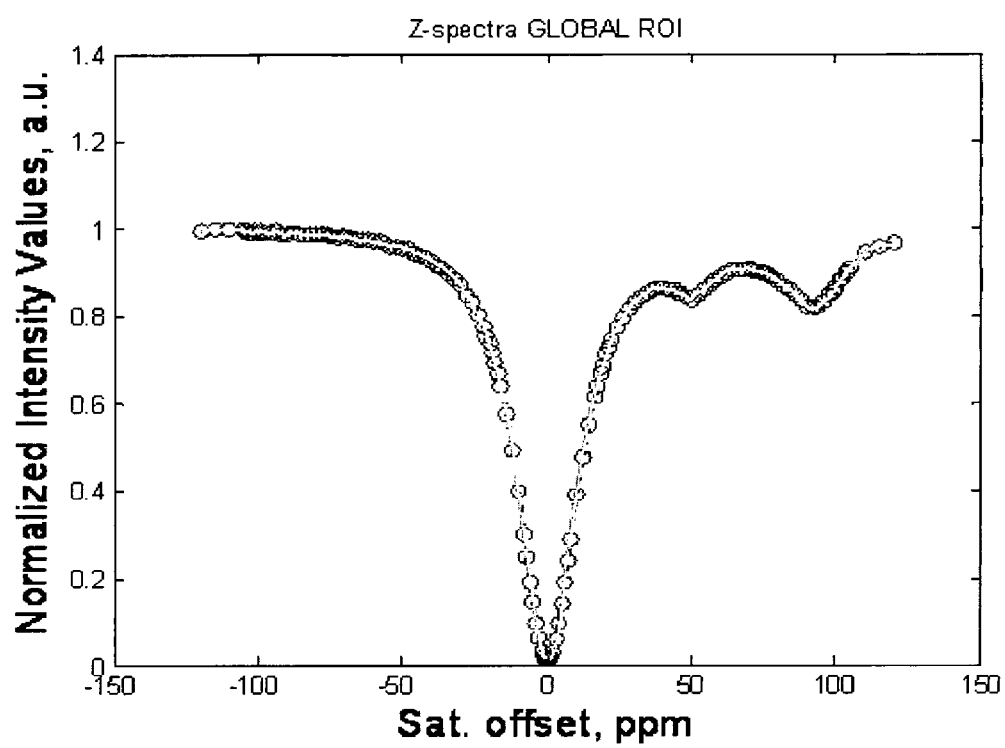
FIG. 14: Z-spectrurm acquired at 7 T of a solution of Compound 2, at pH 5.8 and 298 K.
Figure 15:
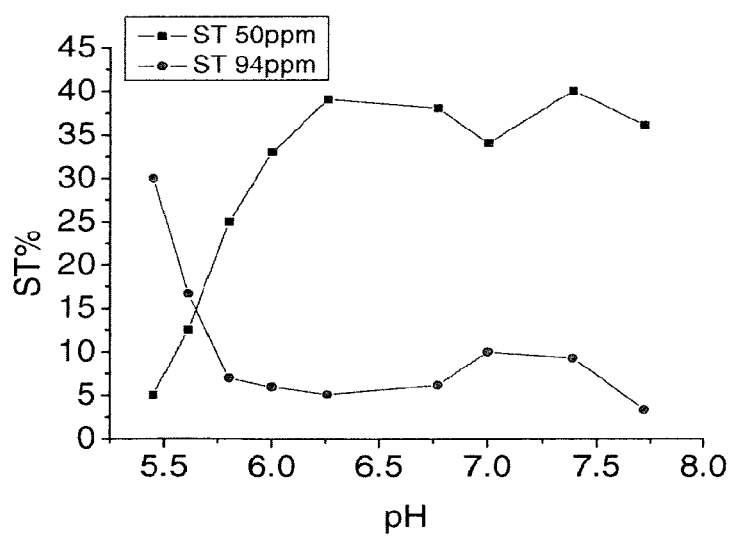
FIG. 15: Dependence from pH of the ST effect obtained upon irradiation of the hydroxilic protons of the two magnetically non-equivalent isomers displayed by Compound 2 (at 20° C.). (calibration curves).
Figure 16:
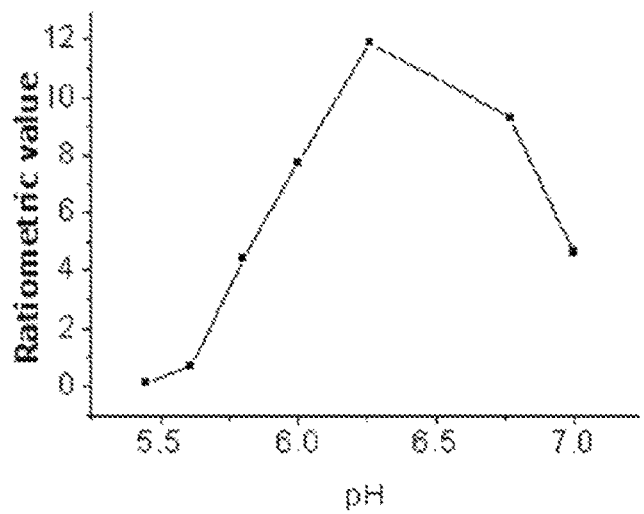
FIG. 16: ratiometric curve reporting the dependence from pH of ST (ratiometric values) resulting by application of the ratiometric approach to ST curves of FIG. 15.

The Z-spectrum of Compound 2 (reported in FIG. 14) shows two regions of saturation transfer that are attributable to the two major diasteroisorners of the complex inside the solution. The presence of two distinct diasteroisomers provides for two suitably shifted OH proton resonance, respectively at 50 and 94 ppm, Responsiveness tests performed with this complex confirmed its sensitivity to the pH that, as it appears frorn FIGS. 15 and 16, is higher at more acidic pH, preferably ranging from 5.5 to 6.2, due to a higher exchange rate shown by the hydroxilic protons of the diasteroisomers of this complex, over the mobile protons the Yb(III)HPDO3A.

A further example of pH responsive agent according to the invention is represented by the Yb$^{3+}$ complex of the 1-(2-hydroxyethyl)-1,4,7,10-tetraazaciclododecan-4,7,10-triacetic acid, hereinafter Compound 3, having formula

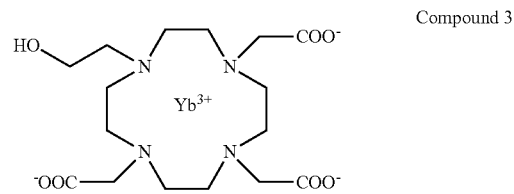

Compound 3

Figure 17:
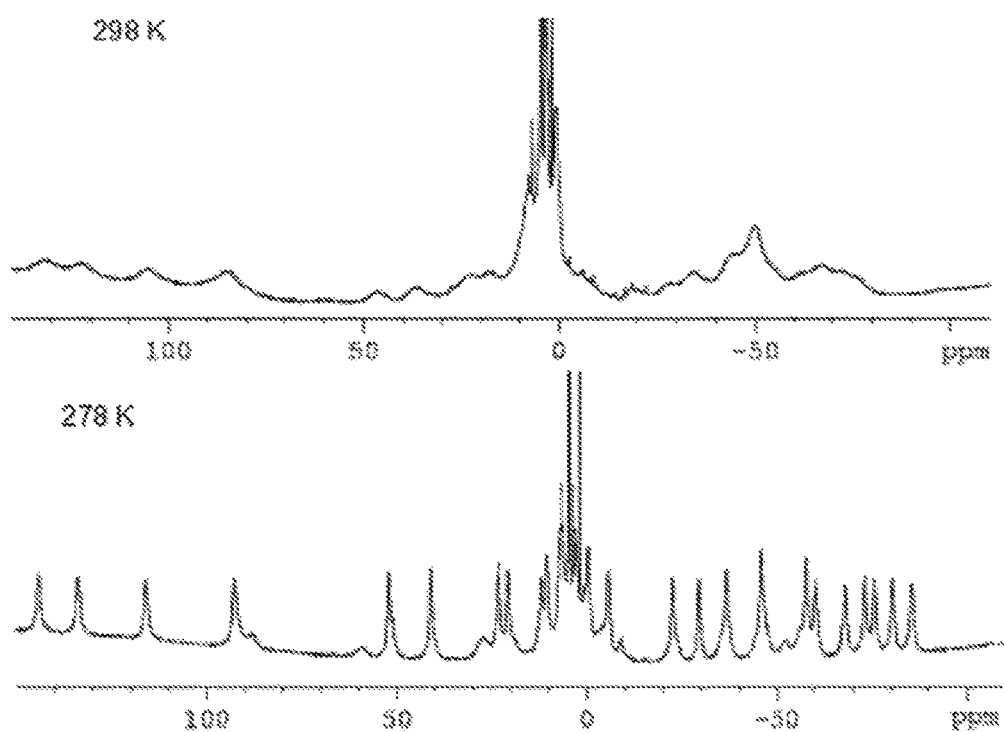
FIG. 17: Comparison from $^1$H NMR Spectra of Compound 3 recorded in $D_2O$ at 278 K and 298 K, and 600 MHz of magnetic field. The high resolution spectrum recorded at lower temperature clearly shows the presence of two sets of signals due to the two major isomers (SAP and TSAP) within the solution. These same signals are much broader at room temperature.
Figure 18:
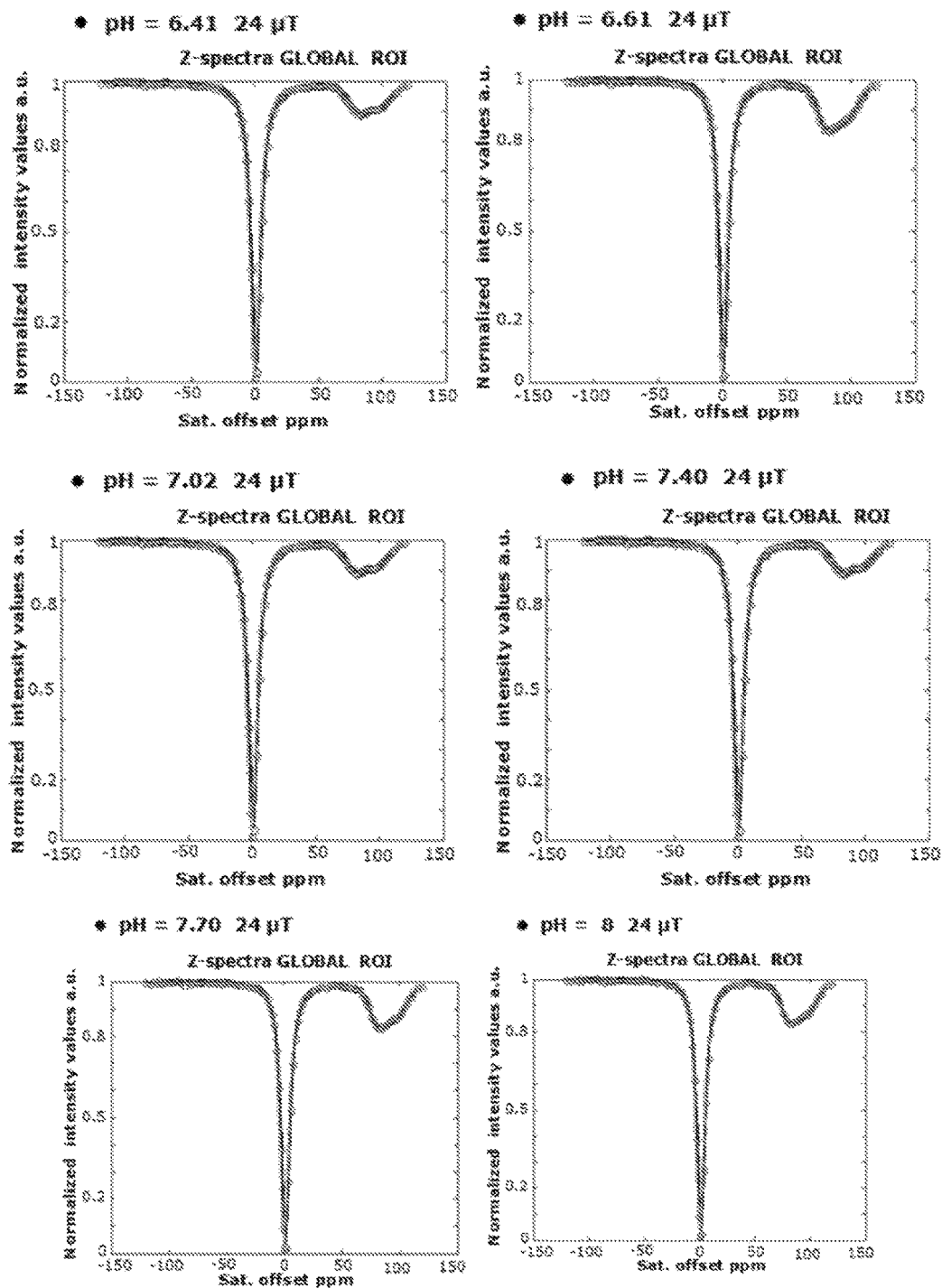
FIG. 18: Z spectra of the Compound 3, recorded from solutions (20 mM) in buffered at different pH values ranging from 6.41 to 8, 20° C.; magnetic field 7 T, irradiation power 24 µT.

The NMR spectrum of this compound, reported in FIG. 17, shows two sets of signals ascribable to the presence of two major isomers, corresponding to the SAP and TSAP forms of the compound. Indeed, four isomers are present in solution differing either in the layout of the acetate arms or in the conformation of the macrocyclic ring. Since these isomers are couple of enantiomers, two set of signals are actually expected in the NMR spectrum as enantiomers are indistinguishable from an NMR point of view. In full agreement with the above, the Z-spectrum of Compound 3 (reported in FIG. 18 for each of the tested pH values) shows the presence of two saturation regions attributable to the OH groups on the hydroxyethyl arms of the two different square antiprism and twisted square antiprism (SAP and TSAP) isomers provided by this compound, which resonance are shifted at 78 and 99 ppm, respectively, The results of responsiveness test performed with this compound in a range of pH ranging from 6.4 to 8, provided in FIG. 18, confirm its sensitivity toward pH.

Another example of Ln(III) complex compound according to the invention is the Yb(III) complex of the 1[2,3-dihydroxy-3-aminepropyl]1,4,7,10-tetraazacyclododecane-4,7,10-triacetic acid (hereinafter Compound 4) having the following formula

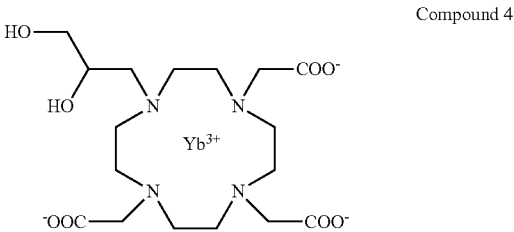

Compound 4

In this case, the presence of two distinct diasteroisomers should provide for four non-equivalent mobile protons, belonging to the two different hydroxyl —OH groups on each the two different SAP and TSAP isomers.

Indeed, the Z-spectrum and the Saturation Transfer ST profiles, of Compound 4 (reported in FIG. 19) confirm the presence of three suitably shifted proton resonances, at 10, 75, and 100 ppm, respectively. Of them, the highly shifted resonances (at 75 and 100 ppm, respectively), are reasonably attributable to the exchanging, protons of the OH groups closest to the coordination sphere of the metal centre provided by the two distinct isomers (SAP and TSAP) of the compound in the solution, while the less shifted signal is ascribable toan exchanging proton of the remaining OH group, more distant from the metal centre. A fourth exchanging pool is undetectable in the spectrum, probably due to its too fast exchange rate on the NMR timescale.

Figure 19:
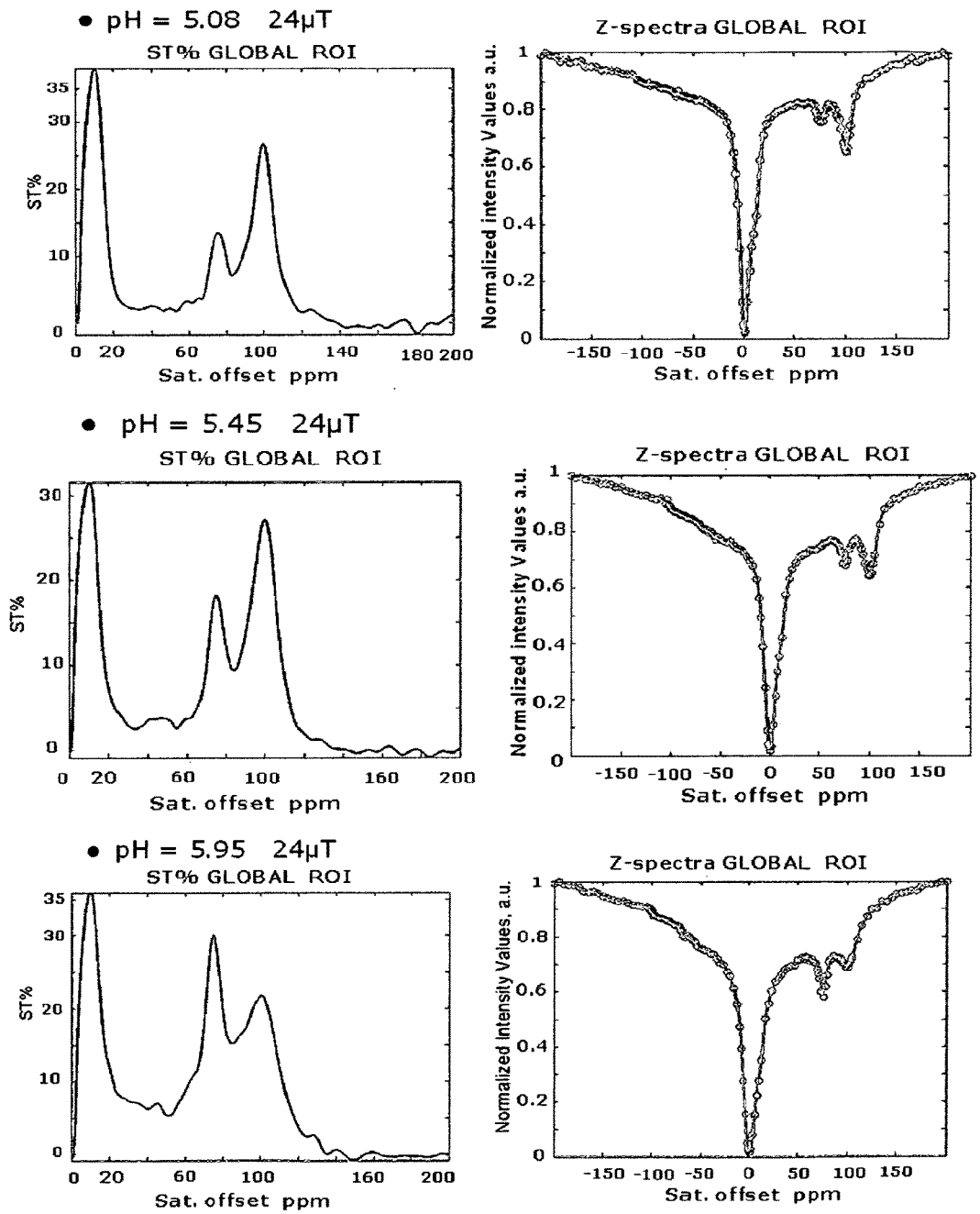
FIG. 19: Saturation Transfer ST profiles (left) and corresponding Z-spectra (right) obtained from aqueous solutions (20 mM) of Compound 4 buffered at different pH values ranging from 5.08 to 6.30, at 293 K, magnetic field 7 T, irradiation power 24 µT.

Responsiveness tests performed in vitro with this complex compound confirm its sensitivity to the pH as it appears from FIGS. 19 and 20.

In particular, obtained results confirm that the dependence of the saturation transfer from the pH displayed by the OH mobile protons of the two diasteroisomers, respectively at 75 ppm and 100 ppm, is different. This allowed the exploitation of a ratiometric approach enabling a concentration -independent assessment of the intracellular pH in test performed with murine macrophagic cells (J774) labeled with this complex compound yielding a pH value of 6.8.

As an additional example, Yb complex of 1[1,3,4-trihydroxybutan-2-yl]1,4,7,10-tetraazacyclododecane-4,7,10-triacetic acid, (hereinafter compound 5) having the, following structure

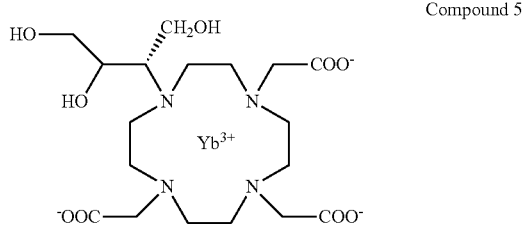

Compound 5 have been investigated.

In this respect, it is worth nothing that the $Gd^{3+}$ complex of this same chelating ligand is a well known contrast agent, clinically approved for use in conventional MRI imaging and marketed as GADOVIST®. Its preparation is described in EP0448191.

The structure of this compound includes two chiral centers significantly increasing the number of potential steroisomers over, for instance, Yb(III)HPDO3A.

Figure 21:
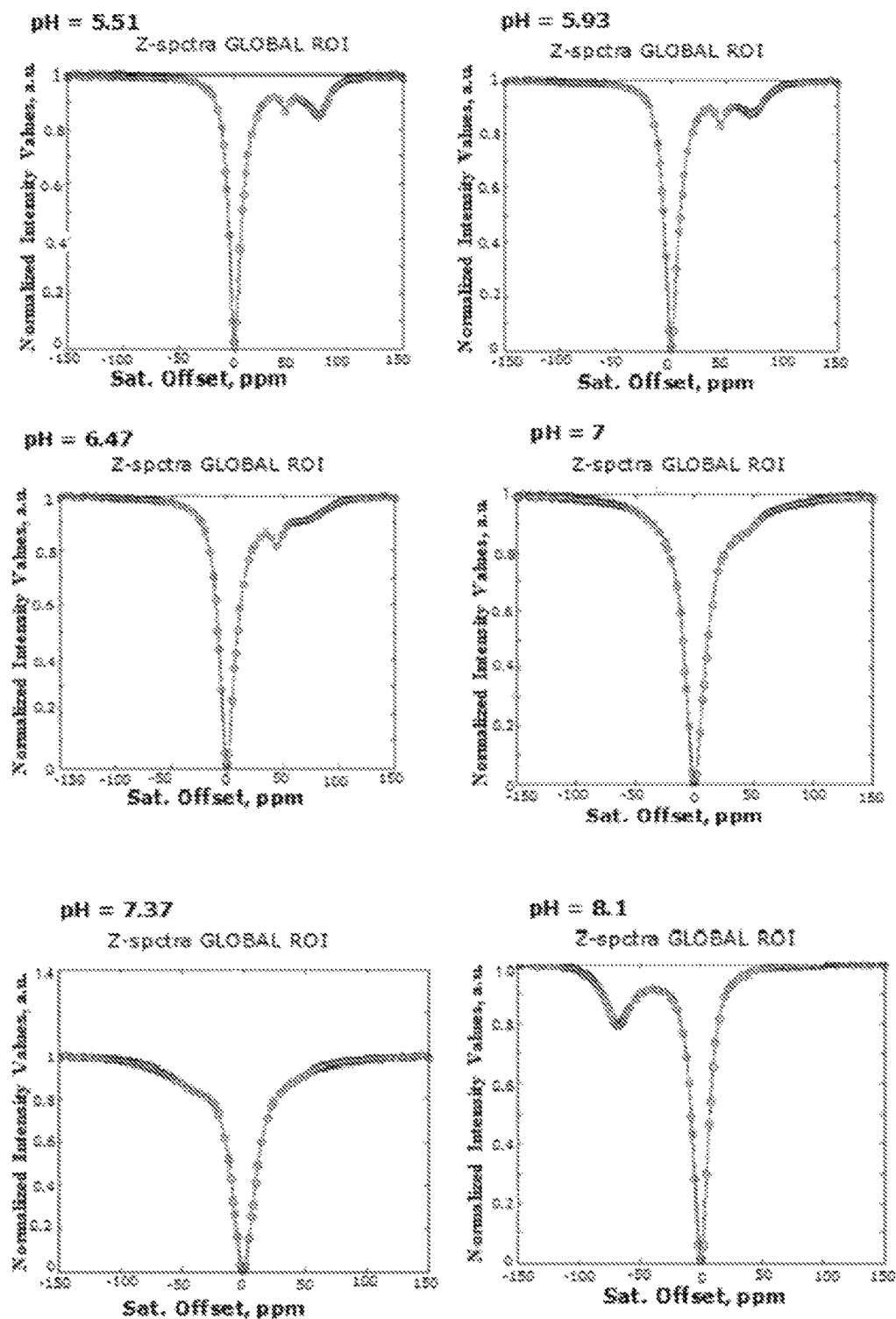
FIG. 21; Z spectra of Compound 5, recorded from aqueous solutions (20 mM) buffered at different pH values, ranging from 5.5 and 8.1, 20° C.; magnetic field 7 T, irradiation power 24 µT.

The spectrum Z of this compound, provided as FIG. 21, shows at least 2 peaks distinguishable at 50 and 75 ppm, respectively, that are due to the two most abundant steroisomeric forms among the plurality it permits.

The high exchange rate characterizing the mobile protons of this cor npound results in that the most abundant NMR-distinguishable isomers are detectable only at lower pH values, around 5.5. At higher pH values a peak at −75 appears, instead, in the spectrum, likely due to a change in the compound structure Though not encompassed by the Lanthanide(III) complexes of formula (I) preferred according to the present invention, the above Compound 5 provides for non-equivalent mobile protons belonging to hydroxyl groups of NMR distinguishable steroisorners of the agent within the solution, consenting to set up a concentration independent CEST imaging procedure according to the present invention.

Accordingly, the use of a Lanthanide (III) complex of the 1[1,3,4-trihydroxybutan-2-yl]1,4,7,10-tetraazacyclododecane-4,7,10-triacetic acid in a ratiometric-based CEST imaging procedure according to the invention, as well as a ratiometric based CEST MRI procedure exploiting two magnetically nor equivalent mobile protons provided by two NMR -distinguishable isomers of the said Ln(III) complex are comprised within the present invention and constitutes an adtlitional embodiment thereof.

EXPERIMENTAL SECTION

The chelating ligands of formula (I) are known in the art or may be easily prepared according to known procedures or synthetic pathways well known to a skilled artisan.

Non limiting examples of synthetic procedures are, moreover, included below, for instance in Examples 1-3, together with details concerning the use of the lanthanide (III) complex compounds according to the invention in ratiornetric-based CEST imaging procedure.

CEST Imaging Procedure and Conditions

CEST MR contrast enhancement have been determined on images acquired at 7 T on a Bruker Avarice 300 spectrometer equipped with a Micro 2.5 microimagmg probe. A typical RARE spin-echo sequence (rare factor 64) with an echo time of 3.3 ms and a TR value of 5 s were used. An acquisition matrix of 64×64 with a square FOV of 10 mm was used. The whole sequence was preceded by a saturation scheme consisting of a continuous wave pulse 2 s long with a RE intensity of 24, 12 6 µT. The Z-spectra were successively analyzed in order to determine the ratiometric value by using a software compiled in MATLAB platform operating, broadly, as disclosed in *Development and validation of a smoothing-splines-based correction method for improving the analysis of CEST-MR images*, Stancanello J Terreno E, Delli Castelli D, Cabella C, Uggeri F 1, Aime S.; CONTRAST MEDIA & MOLECULAR IMAGING Volume: 3, Issue: 4, Pages: 136-149, 2008; and in *Methods for an improved detection of the MRI-CEST effect*. Terreno E, Stancanello J, Longo D, Delli Castelli D, Milone L, Sanders HMHF, Kok M B, Uggeri F, Aime S; CONTRAST MEDIA & MOLECULAR IMAGING; Volume: 4; Issue: 5; Pages: 237-247; 2009 that are ail herein included by reference. The total paramagnetic concentration of the solution was determined through the measurement of magnetic susceptibility of the solution on a Bruker Avance 600 spectrometer (12T).

Example 1

Preparation of the $(Yb^{3+})_4HPDO3A$-Tetramer.

The tetrameric chelated complex YbHPDO3A-tetramer has been prepared by using the synthetic procedure schematized in Scheme 2, whose main steps are detailed below.

Scheme 2
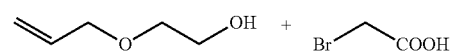
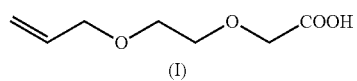
(I)
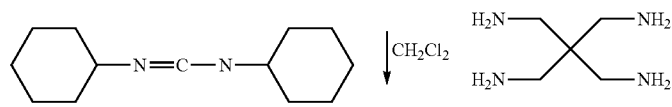
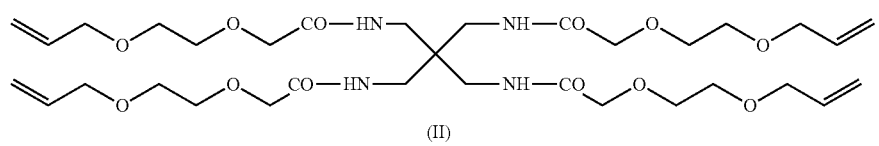
(II)
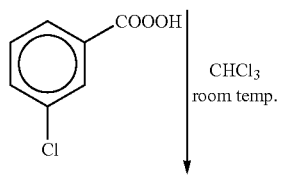
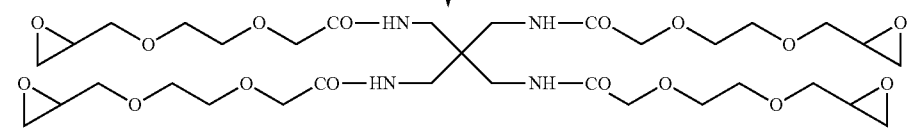
(III)
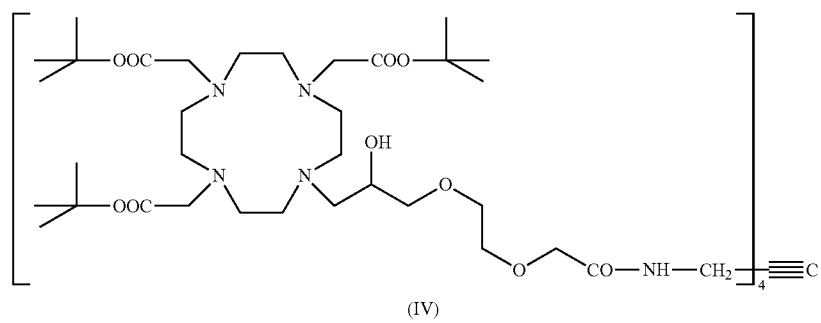
(IV)
TFA | room temp.

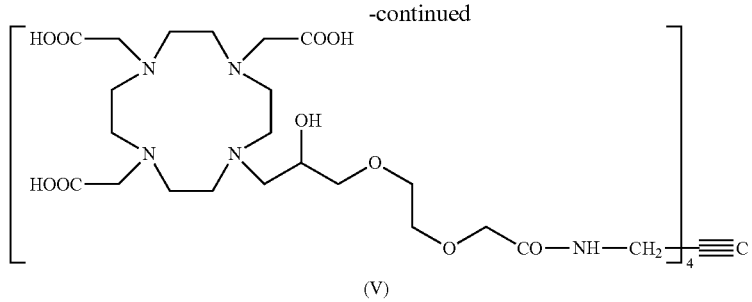

(V)

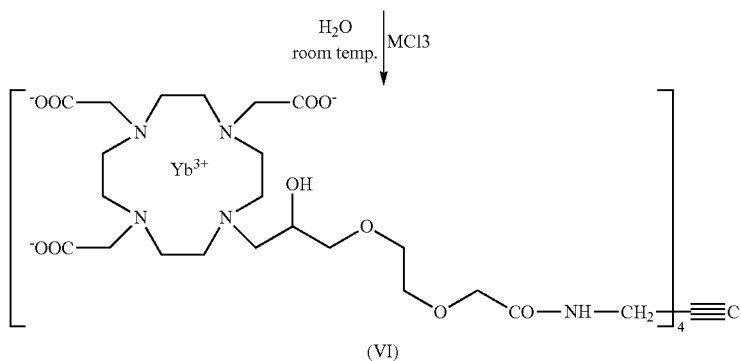

(VI)

3,6-dioxa-8-nonenoic add (I): A solution of 2-allyloxietanol (112 g; 1.1 mol) in THF (100 ml) was dripped in a suspension of sodium hydride (60% in oil) (88 g; 2,2 mol) in THF (250 ml) under mechanic stirrer. After 20 h at room temperature, a solution of bromoacetic acid (138.9 g; 1.0 mol) in THF (150 ml) was added dropwise, causing the spontaneous reflux of the solvent. The solution was kept under reflux for 2 hours, then diluted with ethanol (50 ml) and, after 30 min, the suspension was concentrated. The residue was solved on water (400 ml) and the solution was washed with ethyl ether (3×100 ml), dichloromethane (2×100 ml); the aqueous phase was acidified to pH 1 with hydrochloride acid 37% and the product was extracted with dichloromethane (300 ml+4 50 ml). The organic phase was washed with water (4×50 ml), brine (40 ml) and evaporated to a liquid residue that was distilled under vacuum, at a pressure of 67 Pa, to obtained 3,6-dioxa-8-nonenoic acid (I) as colourless liquid (119.5 g; 0.746 mol). Yield 75%, p.eb$_{67-Pa}$ 98-100° C. Title 93.5%.

12,12'-bis[2-aza-3-oxo-5,8-dioxa-11-undecanyl]-1,13-diene -4,7,17,20-trioxa-9,15-dioxo-10,14-diazatricosane (II)

3,6-Dioxa-8-nonenoic acid (I) (40.1 g; 0.25 mol), diisopropylethylamine (42.6 ml; 32.4 g; 0.25 mol) and O-(benzyltriazol-1-yl)-N,N,N',N'-tetramethyluronium hexafluorophosphate [HBTU] (96.0 g; 0.25 mol) were added to suspension of 2,2'-bis-aminomethylen-1,3-diaminopropane (7.2 g; 0.050 mol) in dimethylformarnide (200 ml). After five days the solution was evaporated to residue (200 g) that was treated with ethyl ether (4×400 ml, 4×50 ml); the ether solution was washed with 5% NaHCO$_3$ solution (6×50 ml), con brine, and evaporated to a residue (84.6 g) that was treated with water (2×100 ml) and then dried under high vacuum (50 Pa) to get 12,12'-bis[2-aza-3-oxo-5,8-dioxa-11-undecanyl]-1,13-diene-4,7,17,20-trioxa-9,15-dioxo-10,14-diazatricosane (II) as solid residue (34.5 g).

12,12'-bis[2-aza-3-oxo-5,8-dioxa-10,11-oxiranundecil]-(1,2)(22,23)-dioxiran-4,7,17,20-trioxa-9,15-dioxo-10,14-diazatricosane (III)

A solution of m-chloroperbenzoic acid (70.5%) (MCPBA) (36.9 g; 0.150 mol) in chloroform (500 ml) was separated from water and dropped into a solution of 12,12'-bis[2-aza-3-oxo-5,8-dioxa-11-undecanyl]-1,13-diene -4,7,17,20-trioxa-9,15-dioxo-10,14-diazatricosane (II) (17.5 g; 0.025 mol) in chloroform (300 ml) under stirrer, After two days to room temperature, the solution was washed with 5% NaHCO$_3$ solution until complete removal of both m-chloroperbenzoic and m-chlorobenzoic acids, then with water and brine. The organic solution was evaporated to residue giving 12,12'-bis[2-aza-3-oxo-5,8-dioxa-10,11-oxiranundecyl]-(1,2)(22,23)-dioxiran-4,7,17,20-trioxa-9,15-dioxo-10,14-diazatricosane (III) as a wax-like solid (20.0 g).

1,23-bis[4,7,10-triacetic[1,4,7,10-tetraazacyclododecan-(1)-yl)]]-12,12'-bis[11[4,7,10-triacetic)-[1,4,7,10-tetraazacyclododecan-(1) -yl]]2-aza-3-oxo-5,8-dioxy-10-hydroxyundecanyl]2,22-dihydroxy -4,7,17,20-tetroxy-9,15-dioxo-10,14-diazatricosane (V)

A solution of 12,12'-bis[2-aza-3-oxo-5,8-dioxa-10,11-oxiranundecil]-(1,2)(22,23)-dioxyran-4,7,17,20-trioxa-9,15-dioxo-10,14-diazatricosane (III) (3.6 g; 0.0047 mol), 1,1-dimethyletyl tris-ester of 1,4,7,10-tetraazacyclododecane-1,4,7-triacetic acid (10.3 g; 0.020 mol) and diisopropylethylamine (4.0 ml; 0.047 mol) in acetonitrile (50 ml), was heated at 50° C. for ten days. The solution was evaporated to give 1,23-bis[4,7,10-tris(1,1-dimethyletylacetate)[1,4,7,10-tetraazacyclodecan-(1) -yl]]-12,12'-bis[11[4,7,10-tris(1,1-dimethyletylacetate)[1,4,7,10-tetraazacyclodecan-(1)-yl]]-2-aza-3-oxo-5,8-dioxy-10-hydroxyundecanyl]-2,22-dihydroxy-4,7,17,20-tetroxy-9,15-dioxo-10,14-diazatricosane (IV). The crude residue was cooled with an ice bath; trifluoroacetic add (20 ml) was added on stirrer; at the solution trisisopropylsilane (100 mcl) was added. After five days, ethyl ether (200 ml) was added and the precipitate was filtered and dried (13.4 g), The solid was solved in water (15 ml) and purified by chromatography on Amberchrome CG161 (2.6×55 cm) (AKTA FPLC) by using methanoi/water as eluent (gradient from 0 to 100% v/v). After freeze-drying of the pure fraction the desired product (V) was obtained a white solid (4.4 g);

Complexometric Title=74% (with zinc sulphate 0.1 N and murexide at pH 10) the main impurity being represented by trifiuoroacetic acid.

The NMR ($^{13}C$) spectrum of the obtained product is consistent with the structure of the chelating ligand. 1,23-bis[4,7,10-triacetate[1,4,7,10-tetraazacyclododecan-(1)-yl)]]-12,12'-bis[11[4,7,10-triacetate)-[1,4,7,10-tetraaza-cyclododecan-(1) -yl]]2-aza-3-oxo-5,8-dioxy-10-hydroxyundecanyl]2,22-dihydroxy -4,7,17,20-tetroxy-9,15-dioxo-10,14-diazatricosane tetra Ytterbium complex (1:4) (VI);

A solution of Ytterbium chloride hexahydrate (3.92 mol) in water (25 ml) was added to solution of the ligand (V) (3.5 g; 0.98 mmol; the exact molar mount of ligand was determined by complexometric titration) in water (100) on stirrer, the solution was very slowly neutralized to pH 7.0 with sodium, hydroxide 2N (11.4 ml). When the ligand excess was <0.2%, and the pH was constant, the solution was desalted by Sephadex G10 column to give, after solution freeze-drying the desired complex, 1,23-bis[4,7,10-triac-etate[1,4,7,10-tetraazacyclododecan-(1)-yl]]-12,12'-bis[11 [4,7,10-triacetate)-[1,4,7,10-tetraazacyclododecan-(1)-yl]] 2-aza-3-oxo-5,8-dioxy -10-hydroxyundecany]2,22-dihydroxy-4,7,17,20-tetroxy-9,15-dioxo-10,14

Example 2

Preparation of the Ytterbium Chelate Complex of the 1(2-hydroxyethyl) -1,4,7,10-tetraazacyclododecane-4,7,10-tri-acetic Acid (Compound 3)

The Ytterblum chelated complex corresponding to Compound 3 has been prepared by using the general synthetic procedure schematized in Scheme 3, whose main steps are detailed below

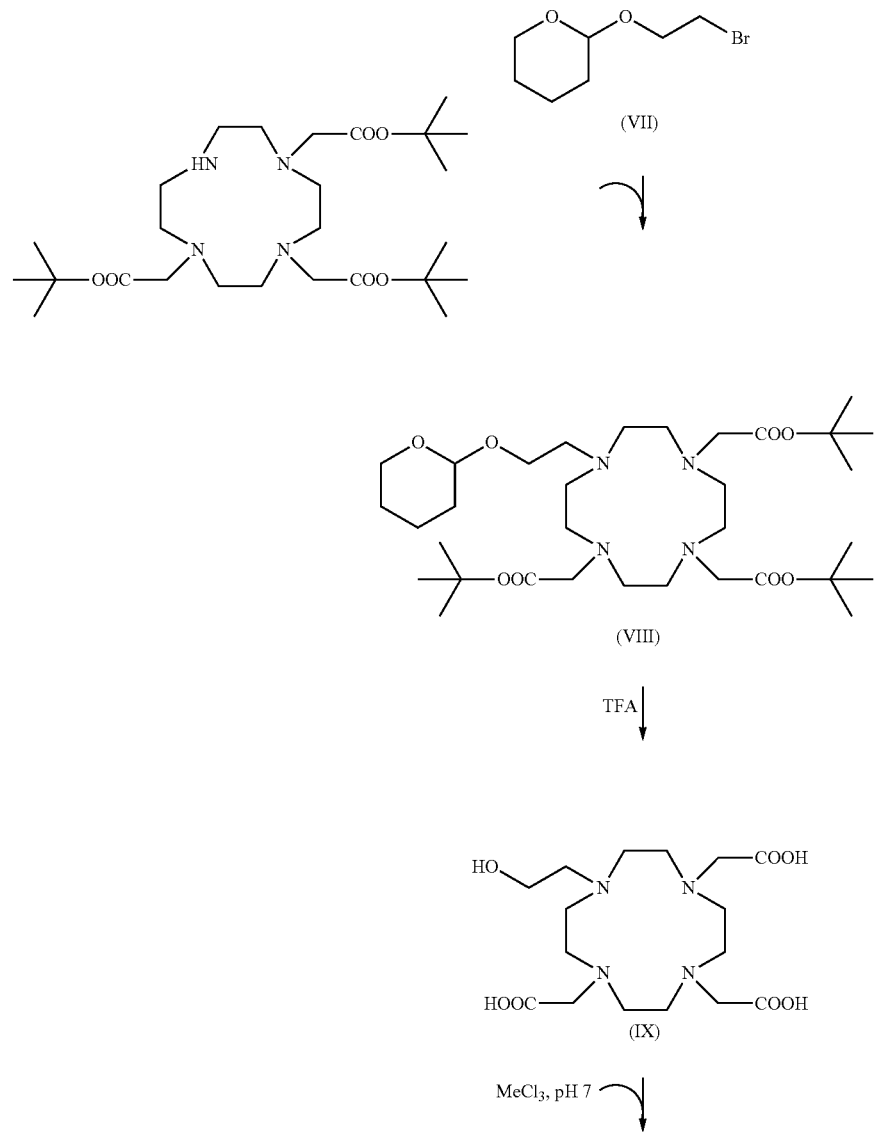

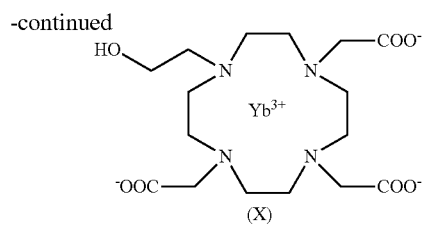

1-[2-[tetrahydropyrane-(2-yl)-oxo]ethyl]-1,4,7,10-tetraazaciclo-dodecan-4,7,10-triacetic-(1,1-dimethylethyl ester) (VIII)

(2-Bromoethoxy)tetrahydropyrane (VII) was synthesized according to the procedure described in J.Org. Chem. 1986, 51, 752-755. This substrate (27.5 mmol; 5.75 g) was dissolved in 50 ml of acetonitrile and added dropwise to a suspension of $K_2CO_3$ (75 mmol; 10.37 g) and DO3A-tris-tert-butylester bromohydrate prepared, for instance, as disclosed in WO96/28433 (25 mmol; 14.89 g) in acetonitrile (150 ml). After one night at room temperature the mixture was filtered and evaporated. The residue was then dissolved ethyl acetate (100 ml) and washed with water and BRINE. The organic solution was concentrated in vacuum and the crude product was purified by chromatography on silica gel with ethyl acetate/ethanol gradient. Fractions containing the product were combined and evaporated to give a yellow oil (8.1 g; yield 49%).
$^1$H-NMR (600 MHz, $CO_3Cl$) and $^{13}C$ NMR (150 MHz, $CD_3Cl$) are consistent with the proposed structure.
MS $[M+H]^+$ calcd: 642.46 found: 643.64.
1-(2-hydroxyethyl)-1,4,7,10-tetraazaciclododecan-4,7,10-triacetic acid (IX)

The intermediate VIII (15 g; 21.5 mmol) was dissolved in water (30 ml), THF (60 ml) and acetic acid (120 ml) and stirred at room temperature for 24 h in order to remove the THP moiety. The mixture was then concentrated and triisopropylsylane (120 µl) and TFA (40 ml) were added dropwise at 0° C. After 3 days at room temperature, the crude product was precipitated with diethyl ether (200 ml), filtered off and purified by liquid chromatography on Amberchrom CG161 resin with 0.2% TFA in water, Fractions containing the desired product were then combined and freeze-dried, acidified with HCl 1N (60 ml) and freeze-dried again (7.3 g; yield 80 %).
$^1$H-NMR (600 MHz, $D_2O$) and $^{13}C$ NMR (150 MHz, $D_2O$) are consistent with the proposed structure.
MS $[M+H]^+$ calcd: 390.21 found: 391.53.
1-(2-hydroxyethyl)-1,4,7,10-tetraazaciclododecan-4,7,10-triacetate (3-) methalate (X)

The complexation reactions were performed with $MeCl_3$ (Me=Yb, Eu, Tm or Dy) in aqueous solution at pH 6.5 by the method of the addition of ligand (See, J. Med. Chem. 2006, 49, 4926) An equimolar amount of aqueous $MeCl_3$ solution was slowly added to the aqueous solution of IX maintaining the pH value at 6.5 with NaOH 0.1 N. The mixture was stirred at room temperature until the pH remained constant. When a little excess of metal was reached, monitored with the orange xilenol assay, (see Contrast Med. Mol, Imaging 2006, 1, 184) a small excess of ligand was added (<2%). The complexes were then desalted by size exclusion chromatography and freeze-dried.

The title of complex, determined by Evans test (D M Corsi, C. P. Iglesias, K. van Bekkum, J A Peters, *Magnetic Resonance in Chemistry*, 2001, 39, (11), 723-726) was 98%.

Example 3

Preparation of the Ytterbium Chelate Complex of the 1[2,3-dihydroxypropyl]-1,4,7,10-tetraazacyclododecane-4,7,10-triacetic Acid (Compound 4)

The Ytterbium chelated complex corresponding to Compound 4 has been prepared by using the synthetic procedure of Scheme 4, whose main steps are detailed below.

Scheme 4

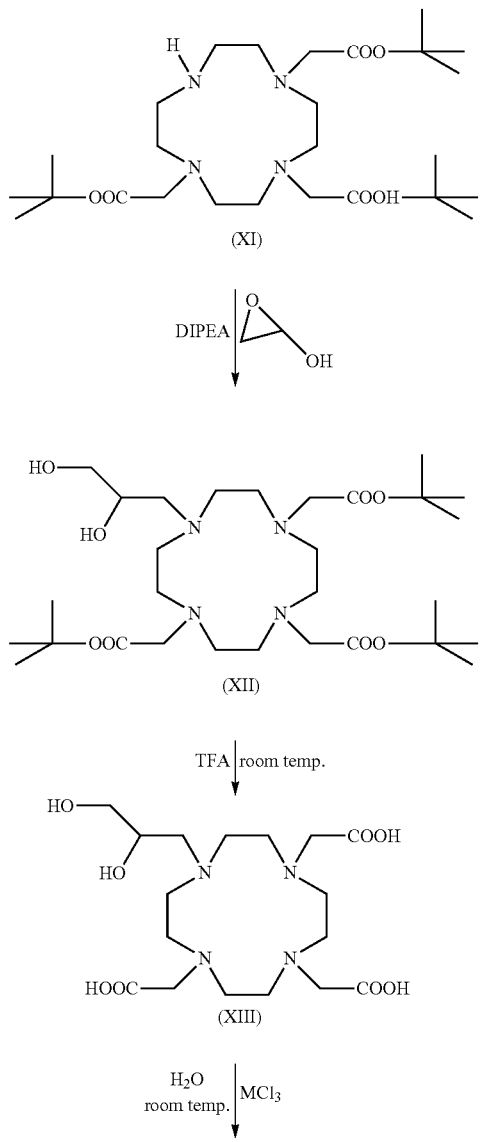

-continued

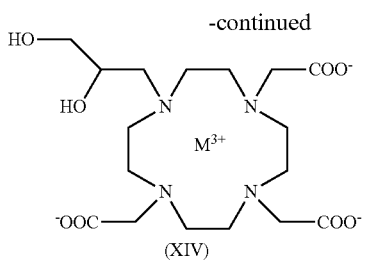

(XIV)

1[2,3-dihydroxypropyl]1,4,7,10-tetraazacyclododecane-4,7,10-triacetate acid (XIII);

A solution of 2,3-epoxypropanol (12.0 g; 0.20 mol), 1,1-dimethyletyl tris-ester of 1,4,7,10-tetraazacyclododecane-1,4,7-triacetic acid (10.3 g; 0.020 mol) (XI) and diisopropylethylamine (8.0 ml; 0.09 mol), in acetonitrile (50 ml), was heated at 50° C. for three days. The solution was evaporated to give 1[2,3-dihydroxypropyl]1,4,7,10-tetraazacycloclodecane-4,7,10-tris(1,1-dimethyletylacetate) (XII). The crude residue was solved in dichloromethane (100 ml) and cooled with ice bath and trifluoroacetic add (15 ml) was then added on stirrer; the dichloromethane was evaporated, trifluoroacetic add (90 ml) and triisopropylsilane (200 μl) was added. After one day, ethyl ether (200 ml) was added and the precipitate was filtered and dried (16.5 g). The solid was solved in water (30 ml) and purified on Amberlite XAD 1600 (5×12 cm) (AKTA FPLC) with water as eluent. After freeze-drying of the pure fraction the desired ligand (XIII) was obtained as white solid; (10.6 g).

The NMR ($^{13}C$) spectrum is consistent with the structure of the chelating ligand.

The complexometric titration of the collected ligand was then performed (with zinc sulphate 0.1N and murexide at pH 10) to assess the amount of Lanthanide oxide requested for its exhaustive complexation.)

Obtained title (41.9%) confirm the residual presence of solvent and trifluoroacetic acid that are removed after complexation of the ligand.

1[2,3-dihydroxy-3-aminepropyl]1,4,7,10-tetraazacyclododecane-4,7,10-triacetate metalate (XIV);

Metal oxide (2.21 mmol) was added to solution of 1[2,3-dihydroxypropyl]1,4,7,10-tetraazacyclododecane-4,7,10-triacetic acid (XII) (4.4 g; 4.43 mmol; calculated by complexometric titration) in water (30 ml) on stirrer, the solution was heated to 90° C. When the oxide was solved, the solution was cooled, filtered un Millipore 0.45 μm and Relite 3ASFB was slowly added to pH 7; the resin was filtered and the solution was freeze-drying to give 1[2,3-dihydroxypropyl]1,4,7,10-tetraazacycloclodecane-4,7,10-triacetate metalate (XIV)

| Metal | Days to 90° C. | obtained compound | Complex title (Evans) | Yield |
|---|---|---|---|---|
| Yb | 3 | 2.31 g | 75.6% | 67.5% |
| Eu | 1 | 2.14 g | 84.5% | 72.0% |

The excess of ligand, was determined by complexometric titration with Metal chloride 0.001 M by using, xylenoleorange as indicator to pH 5.8

The title of complex was instead determined by Evans test (DM Corsi, C. P. Iglesias, H. van Bekkum, J A Peters, *Magnetic Resonance in Chemistry*, 39, 11, pages 723-726, 2001

Example 4

Test in Vitro
Responsivity of Yb(III)HPDO3A Towards pH.

Figure 3E:
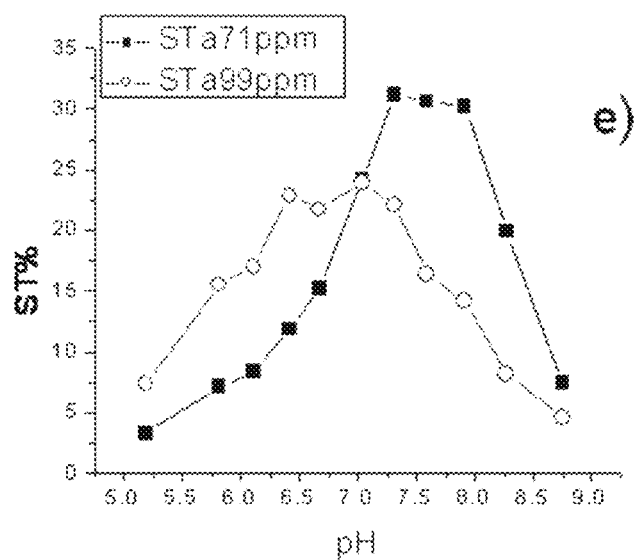
FIG. 3E: variation of the ST effect with variation of the pH obtained upon irradiation of hydroxylic protons of the two isomers, respectively at 72 ppm (square) and 99 ppm (circles) (calibration curves) (24 mM solution, 20° C.; irradiation pulse 24 µT; irradiation time 2 s).
Figure 3F:
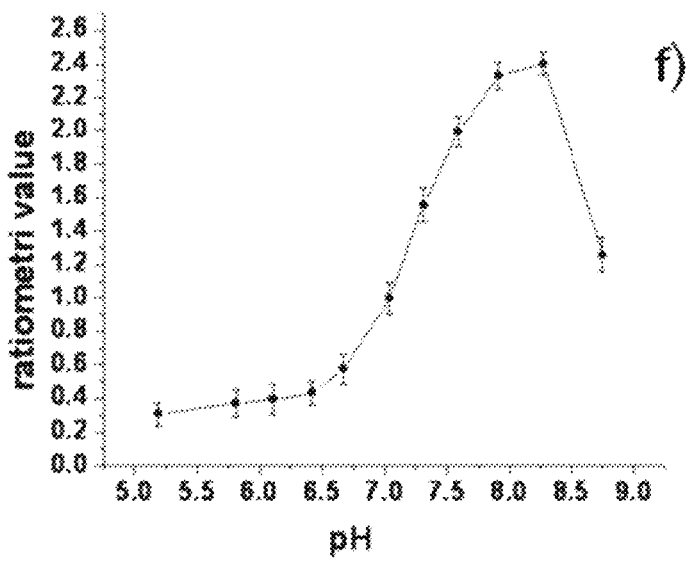
FIG. 3F; ratiometric curve showing the dependence of ratiometric values from pH that results by application of the ratiometric approach to the ST curves of FIG. 3E. In the figure, ratiometric value (shown on the vertical axis (y) of the graph) stands for the value calculated by using the above equation (1) upon irradiation of the mobile proton at 72 ppm (site 1) and 99 ppm (site 2) respectively.

The responsiveness of Yb(III)HPDO3A towards pH has been investigated in vitro by using a phantom containing 14 capillary, of which 11 comprising solutions of YbHPDO3A having 24 mM concentration and different pH, ranging from 5.19 to 8.75 (capillaries 1-11), and 3 containing solutions of YbHPDO3A at pH 7.31 and concentrations ranging from 3 to 24 mM. CEST MRI experiments have been performed at 20° C. and 37° C. MR images of the phantom irradiated at 72 and 99 ppm, respectively, were recorded and shown in FIG. 3. In particular, the FIG. 3c) shows the ST map obtained upon irradiation of the nyclroxilic protons at 72 ppm (20° C.; irradiation power pulse 24 μT), while FIG. 3d) shows the ST map obtained upon irradiation of thehydroxilic protons at 99 ppm (20° C., irradiation power pulse 24 μT).

Obtained results confirms that the dependence from pH of the saturation transfer displayed by each of the OH protons of the two Yb(III)HPDO3A diastereoisomers within the solution is different, wherein this allows the exploitation of a ratiometric approach. Calibration curves have been then performed, reported in FIG. 3e), by measuring the variation of the ST effect with variation of the pH obtained upon irradiation of hydroxylic protons of the two isomers, respectively at 72 ppm and 99 ppm, consenting to obtain the ratiometric curve of FIG. 3f).

Example 5

Use of Yb(III)HPDO3A to Assess the Intracellular pH.

Mesenchirnal stars cells has been chosen as cell line for the test. The cells used in the experiment have been extracted from murine bone marrow, then cultured in Alpha MEM media with 20% of PBS (Fetal Bovine Serum). At first passage primocin is added to cells. When confluence was about 70% cells have been detached with 0.25 tripsin-edta, washed with PBS and resuspended with a solution of YbHPDO3A 0.15 M. Part of the cells have been incubated at 37° C. for 3 hours while part have been eiectroporated. Then cells have been washed in PBS and prepared for the MRI experiment.

In particular: CEST maps (shown in FIG. 5) have been obtained for a phantom containing: 1) a pellet of MSH cells incubated for 3 hours with a solution containing 0.15 M of YbHPDO3A in PBS 37° pH 7.4 (capillary 2); 2) a pellet of MSH cells electroporated with a solution 0.15M of YbHPDO3A in PBS pH 7.4 (capillary 3); 3) a pellet of MSH cells incubated only with PBS and used as reference (capillary 1), and an empty capillary (capillary 4). The ST % effect was measured upon irradiation of the phantom at 72 and 99 ppm respectively. Obtained ST maps reported in FIG. 5B and FIG. 5C, respectively, show that a ST % effect could be seen only for those cells incubated or electroporated with YbHPDO3A, while any saturation was recorded in absence of the complex. The observed ST effect was higher for those cells electroporat, corresponding to a measured pH of 7.00±0.2 while the pH measured in the pellet of incubated cells of capillary 2 was 6.8±0.3.

Example 6

Test in Vivo
Use of Yb(III)HPDO3A for the Assessment of the pH on Animal Model of Melanoma In vivo measurements have been performed upon intravenous injection of 1.2 mmol/Kg of YbHPDO3A in an animal model of melanoma 6 to 10-week old female C57B16 mice (Charles River Laboratories, Calco, Italy) were inoculated subcutaneously in the left flank with 0.2 of a single suspension containing approximately $1 \times 10^6$ B16 murine melanoma cells, obtained from ATCC (Manassas, Va., USA) and grown in DMEM medium (Dulbecco's Modified Eagle Medium) supplemented with 10% FBS, 2 mM glutamine, 100 U/ml penicillin and 100 µg/ml streptomycin.

CEST contrast enhanced MR images were acquired at 7 T on a Bruker it Avance 300 (Bruker, Germany) spectrometer equipped with a Micro2.5 microimaging probe.

The mice were injected with the solution of YbHPDO3A (200 µL of a 150 mM solution of YbHPDO3A, corresponding to a 1.2 mmol/Kg of CEST agent, namely three times the clinically approved dose for ProHance®) 7 days after the cell inoculation, i.e. when the tumor mass reached a mean diameter of about 4 mm.

Figure 6:
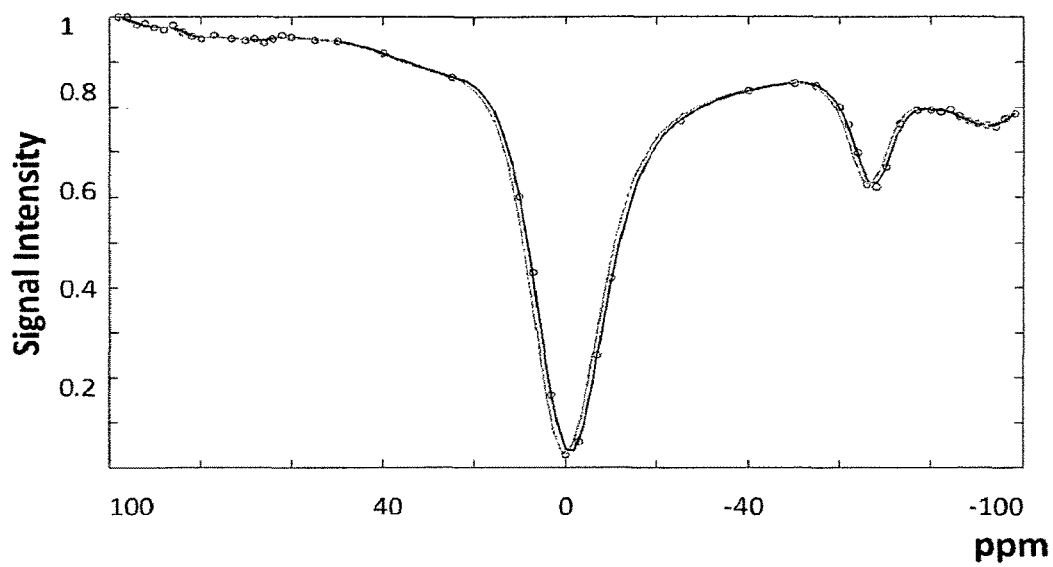
FIG. 6: Z-spectrum obtained from a bladder of a mouse injected with 200 µL of a 150 mM solution of YbHPDO3A, recorded in a Bruker Avance300 spectrometer. In the recorded spectrum the darker line corresponds to the fitting curve and the lighter to the fitting curve translated in order to have the minimum of the Z spectrum corresponding to 0 ppm.
Figure 7:
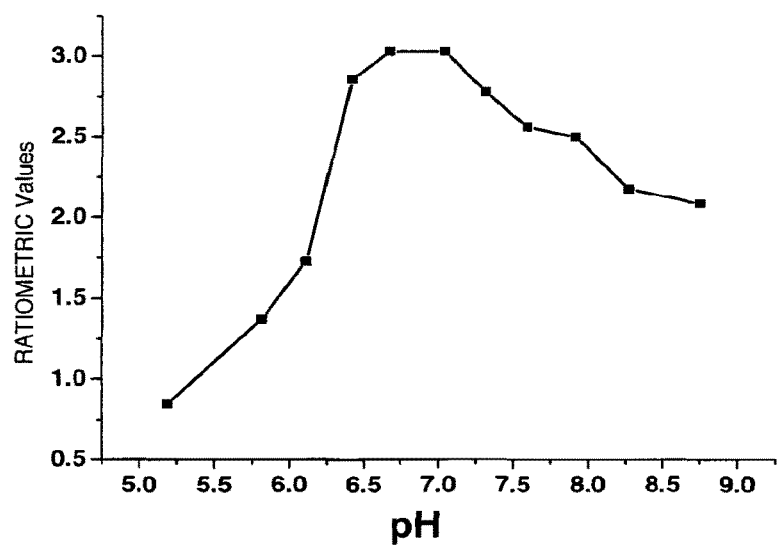
FIG. 7: ratiometric curve of YbHPDO3A measured in vitro at 33° obtained from calibration curves recorded to this temperature, as per Example 6.

The Z-spectra were acquired before and immediately after the i.v, injection of the agent by using a RARE sequence (RARE factor 8, effective echo time 4.1 ms) preceded by a square continuous wave pulse (duration 2 s, power 12 µT, frequency range from −20 to 20 ppm in 1 ppm steps). CEST contrast has been measured in bladder, kidneys and tumor. The Z-spectrum collected in the bladder (reported in FIG. 6) revealed a shift for the exchanging pool corresponding to a physiological T lower (33° C.) than the expected 37° C., due to the anaesthesia. The calibration of the ST dependence from pH has been then repeated at this temperature, by following the procedure formerly described in Example 2. The obtained ratiometric curve in shown in FIG. 7.

The ST effect was then measured in the bladder, kidneys and tumor by application of the ratiometric method, resulting in a pH of 6.06±0.2 in the bladder, 6.24±0.2 in the kidneys medulla, 6.6±0.2 in the tumor region.

In FIG. 8 the calculated ST map in tumor area has been superimposed on the corresponding anatomical image, where appears as lighter area, which is actually bright red in the image appearing on the tomograph display, Example 7

Test in Vitro
Responsive Properties of Yb(III)HPDO3A Towards Temperature.

Figure 4A:
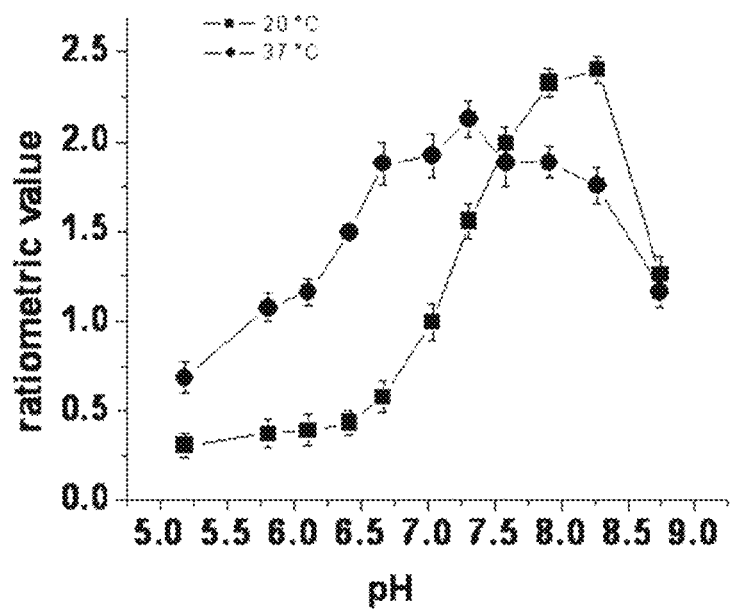
FIG. 4A: Ratiometric curve showing the dependence of the ST effect from Temperature (ratiometric value, obtained by application of the ratiometric approach on ST calibration curves recorded, respectively, at 20° C. (squares) and 37° C. (circles).
Figure 4B:
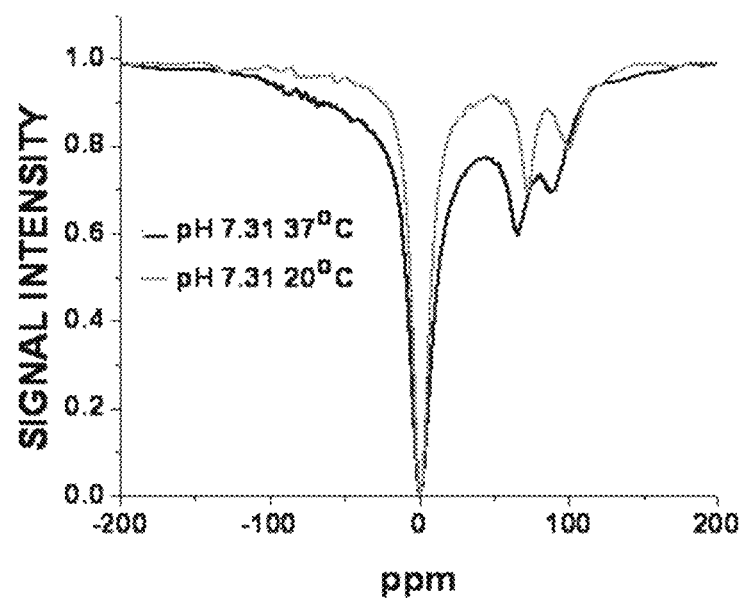
FIG. 4B: Z-spectra of YbHPDO3A (24 mM solution, pH 7.31) recorded at 37° C. (darker line) and 20° C., same pH (gray line) by using an irradiation pulse of 24 µT.

A solution of Yb(III)HPDO3A (24 mM) having pH 7.31 was used for test. The spectra, of of the solution, recorded at 20 and 37° C. respectively, show that the chemical shift of the hydroxylic protons of the NMR distinguishable Yb(III) HPDO3A diasteroisomers within the solution is very sensitive to the temperature. In fact, as shown in FIG. 4B, when passing from 20° to 37° C., the resonance frequencies corresponding to two different the steroisomers of the complex switch from 99 to 88 and from 72 to 64.3 ppm, respectively. Since the proton chemical shift does not depend on the agent concentration, the simple collection of the Z-spectrum allows to determine exactly the temperature of the environment and, then, to determine the pH by means of a suitable in vitro calibration.

Example 8

Responsive Properties of Yb(III)HPDO3A-Tetramer Towards Temperature.

Figure 10A:
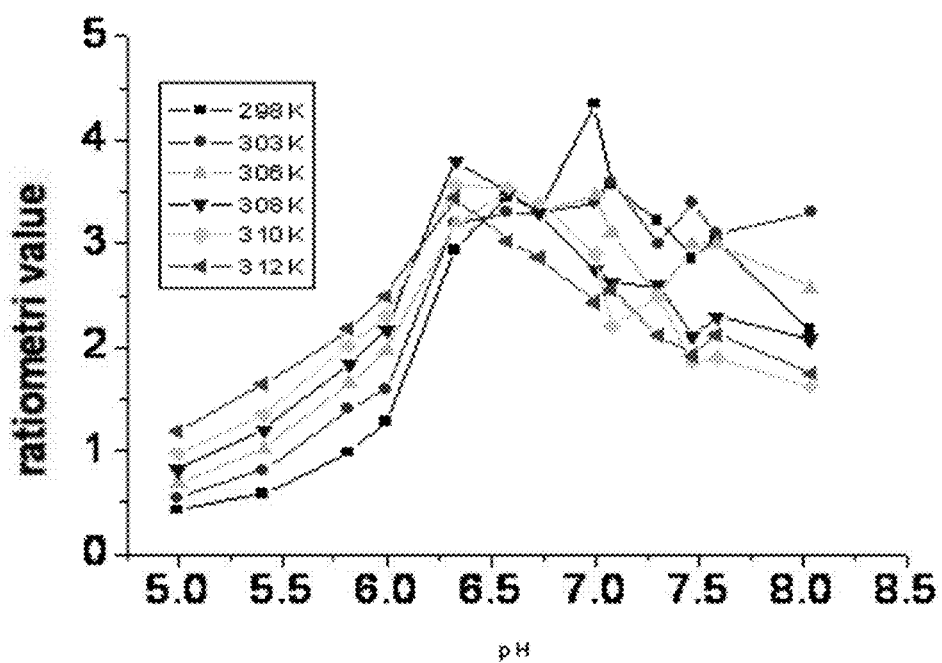
FIG. 10A: ratiometric curves measured at different temperatures, ranging from 298 to 312 K, upon irradiating the hydroxyl protons of two isomer of the YbHPDO3A-tetramer and application of the ratiometric approach.
Figure 10B:
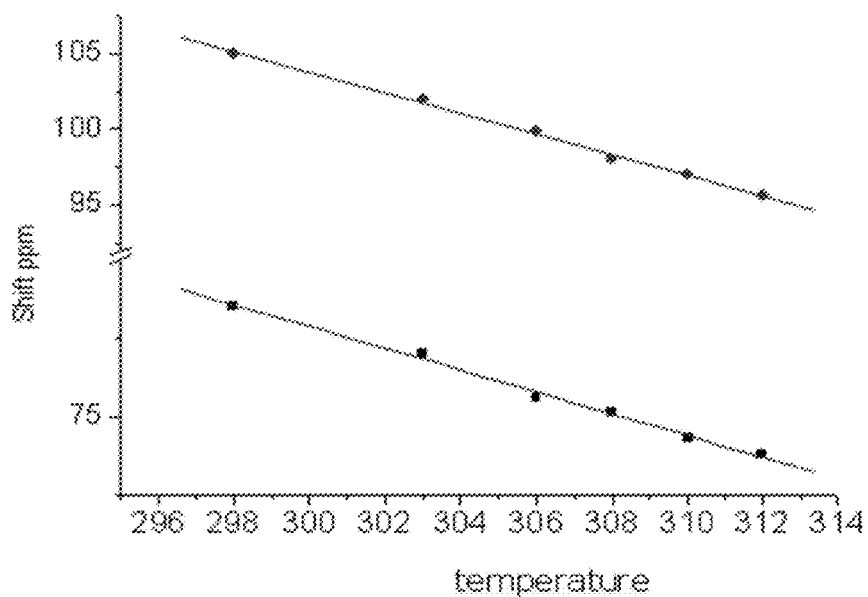
FIG. 10B: dependence from the temperature of the NMR chemical shift of the hydroxylic protons belonging to two NMR-distinguishable isomers of YbHPDO3A-tetramer.
Figure 11:
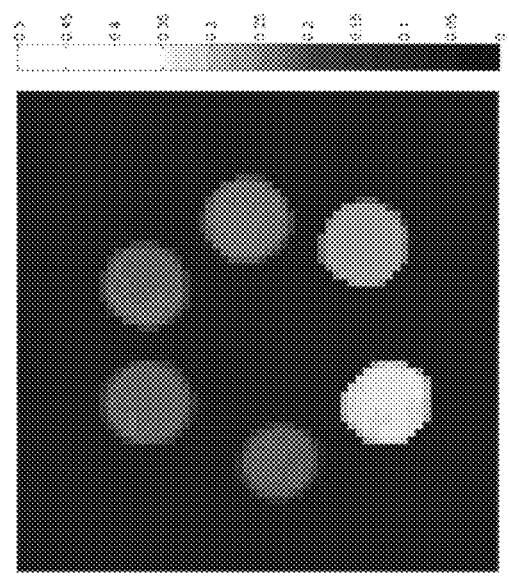
FIG. 11: MRI images of a phantom containing YbHPDO3A-tetramer at different concentrations, ranging from 0.26 to 8.4 mM (pH 7.4 and 298 K). Left $T_2$ weighted Image; right obtained ST map.
Figure 11:
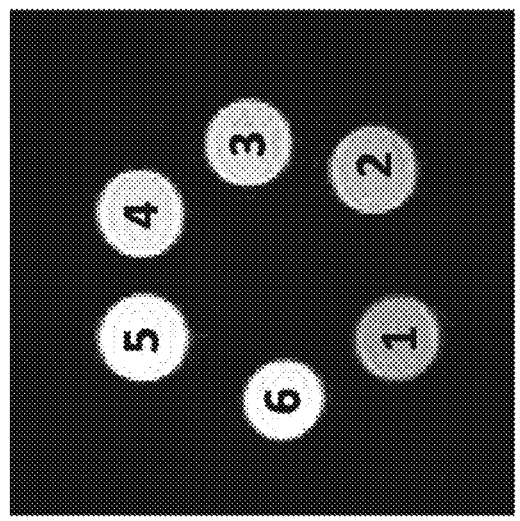

The test was performed with a phantom containing solution of YbHPDO3A-tetramer in serum having, different concentration, ranging from 0.26 to 8.4 mM., pH 7.4 and 298K. The dependence of the chemical shifts of the OH mobile protons (of the tetrameric complex steroisomers) on the Temperature was tested by operating as formerly described for the monomeric compound. Obtained ratiometric curves, displayed in FIG. 10, substantially confirm the results obtained wits the monomeric compound in Example 7. However, as expected, and as appears in FIG. 10B, the sensitivity per molecule of tetrameric complex results greatly increased (when compared with the corresponding monomeric complex).

Example 9

Use of Compound 4 to Assess the Intracellular pH.

Murine macrophagic cells (J774) has been chosen as cell line for the test. The range of sensitivity of the ratiometric curve obtained with this compound was firstly properly tuned in the range of intracellular pH.

In particular, by application of the ratiometric approach to the ST curves calculated over pH upon irradiation of the two more shifted mobile proton pools at 75 ppm (site 1) and 100 ppm (site 2), respectively, consented to obtain the ratiometric curve of FIG. 20, displaying the variation of the ratiometric ST with the pH, in a pH range from 5.5 to 7.

The Compound 4 was internalized into murine macrophagic cells (J774). J774 have been obtained from American Type Culture Collection (ATCC, Manassass, Va. Cells were cultivated in Dulbecco's Modified Eagles's medium (DMEM) supplemented with 10% fetal bovine serum (FBS), 100 U/ml penicillin and 100 mg/ml streptomycin. They were seeded in 75-cm$^2$ flasks at density of ca. $2 \times 10^4$ cells/cm$^2$ and cultivated in a humified 5% $CO^2$ incubator at 37° C. J774 was incubated overnight with 70 mM of compound 4. Cells have been washed and reincubated with their growing medium for 3 hours. The cells were then detached with 0.25% Tripsin-EDTA and prepared for the MRI CEST experiment.

A Ratiometric value of the saturation transfer was calculated by acquiring Z-spectra of a phantom containing pellets of cells either incubated overnight with compound 4 or incubated with the growing medium.

The ST effect observed for incubated cells yielded to a pH value of 6.8.

Example 10

Test in Vitro
Responsivity of Compound 4 towards pH.

The responsiveness of the compound 4 towards pH has been investigated in vitro by using a phantom containing 6 capillary comprising solutions of Ytterbium compiex having 20 mM concentration and different pH, ranging from 5.08 to 7.4. CEST MRI experiments have been performed at 20° C. The Z-spectra collected from the phantom irradiated (irradiation power 24 µT) at 75 and 100 ppm, respectively, are shown in FIG. 19.

The ratiometric ST curve that has been obtained as a function of the pH is shown in FIG. 20.

The invention claimed is:
1. A HPDO3A-Tetramer of formula

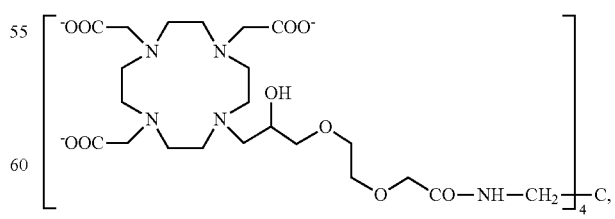

a salt thereof or a chelated complex thereof with a paramagnetic metal ion.

2. A diagnostic composition comprising a $(Yb^{3+})_4$ HPDO3A-tetramer of formula

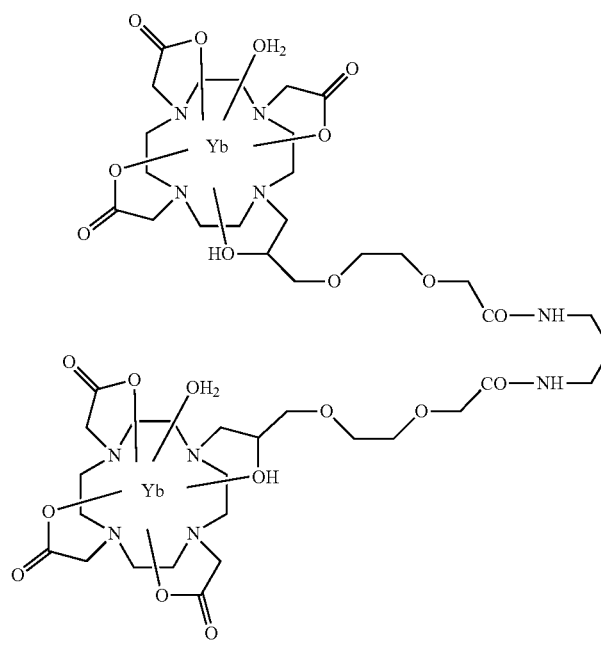
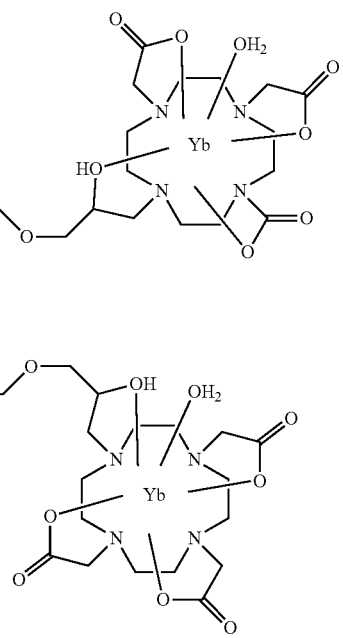
together with suitable physiologically acceptable additives and/or carriers.
* * * * *